United States Patent [19]

Sugiyama et al.

[11] Patent Number: 5,651,991
[45] Date of Patent: Jul. 29, 1997

[54] DRUG CARRIERS

[75] Inventors: Makoto Sugiyama, Kyoto; Atsuhiko Okita, Otsu; Junzo Seki, Ibaragi, all of Japan

[73] Assignee: Nippon Shinyaku Co. Ltd., Japan

[21] Appl. No.: 199,567

[22] Filed: Feb. 22, 1994

Related U.S. Application Data

[63] Continuation-in-part of Ser. No. 902,521, Jun. 22, 1992, abandoned, and Ser. No. 898,168, Jun. 12, 1992, abandoned, which is a continuation of Ser. No. 262,431, Oct. 25, 1988, abandoned, said Ser. No. 902,521, is a continuation of Ser. No. 516,427, Apr. 30, 1990, abandoned, which is a continuation-in-part of Ser. No. 262,431, Oct. 25, 1988, abandoned.

[30] Foreign Application Priority Data

Oct. 28, 1987 [JP] Japan .................. 62-272770

[51] Int. Cl.$^6$ ............... A61K 9/10; A61K 9/107; A61K 9/42
[52] U.S. Cl. ............... 424/502; 424/489; 424/490; 424/499; 514/937; 514/943
[58] Field of Search ............... 424/458, 498, 424/489, 490, 499, 502; 514/937–943

[56] References Cited

U.S. PATENT DOCUMENTS

| | | | |
|---|---|---|---|
| 4,094,965 | 6/1978 | Layne et al. | 424/1.5 |
| 4,384,975 | 5/1983 | Fong | 427/213.36 |
| 4,752,485 | 6/1988 | Sharma et al. | 426/99 |
| 4,840,799 | 6/1989 | Appelgren et al. | 424/493 |
| 4,914,084 | 4/1990 | Ecanow | 514/6 |
| 4,933,183 | 6/1990 | Sharma et al. | 424/439 |
| 5,023,271 | 6/1991 | Vigne | 514/458 |

FOREIGN PATENT DOCUMENTS

| | | | |
|---|---|---|---|
| 126583 | 2/1988 | European Pat. Off. | B01J 13/02 |
| 2814038 | 7/1981 | Germany | A61K 49/02 |

OTHER PUBLICATIONS

Ekman, Stig et al., Chemistry and Physics of Lipids, 45 (1987) 13–25.
Ekman Stig et al., Biochimica et Biophysica Acta 921 (1987) 347–355.
Tajima, Shoji et al., Journal of Biological Chemistry 258 (1983) 10073–10083.
Okabe, Hiromitsu, et al., J. Biochem., 104, 141–148 (1988).
Connelly, P.W., Biochimica et Biophysica Acta, 666 (1981) 80–89.
Granot, Esther, Biochimica et Biophysica Acta, 833 (1985) 308–315.
Yokoyama, Shinji, et al., J. Biol. Chem. 260, 1985, 3155–3163.
Nishikawa, Osamu, et al., J. Biochem., 103, 188–194 (1988).
Miller, Kurt W., et al., Biochemistry, 22(2), 1983, 443–451.
Weinberg, Richard B., et al., Atherosclerosis, 44 (1982) 141–152.
Badr, Mervat, et al., Journal of Colloid and Interface Science, 113, 414–420 (1986).
Burrier, Robert E., et al., Biochemistry, 23, 5366–5371 (1984).
Mims, Martha P., et al., Biochemistry, 27, 5290–5295 (1988).
Mims, Martha P., et al., Biochemistry, 25, 474–483 (1986).
Spooner, Paul J.R., Journal of Biological Chemistry, 263, 1444–1453 (1988).

(List continued on next page.)

*Primary Examiner*—Gollamudi S. Kishore
*Attorney, Agent, or Firm*—Graham & James LLP

[57] ABSTRACT

A drug carrier useful for improved drug delivery upon administration comprising a fat or fatty emulsion as a core and a surface layer thereover wherein the core amounts to 30% to 65% and the surface layer amounts to 35% to 70%. The constituents of the core and surface layer are detailed together with the improved drug delivery obtained. The emulsion has a mean particle diameter less than 100 nm.

8 Claims, 14 Drawing Sheets

OTHER PUBLICATIONS

Maranhao, Raul C., Biochimica et Biophysica Acta, 875, 247–255 (1986).

Ginsberg, Geoffrey, et al., Journal of Biological Chemistry, 259, 6667–6673 (1987).

Ginsberg, Geoffrey, et al., Journal of Biological Chemistry, 257, 8216–8227 (1982).

Craig, Iain F., et al., Journal of Biological Chemistry, 257, 330–335 (1982).

Tall, A.R., et al., Biochimica et Biophysica Acta, 487, 145–153 (1977).

Ekman, Stig, et al., Biochimica et Biophysica Acta, 959, 343–348 (1988).

Ekman, Lipids, 22, No. 9, (1987), 657–663.

FIG.16

|          | Recovery(%) | Uptake(%) |
|----------|-------------|-----------|
| Sample A | 82.9        | 17.1      |
| Sample B | 64.7        | 35.3      |
| Sample C | 41.2        | 58.8      |
| Sample D | 27.9        | 72.1      |

———— 100nm

———— 100nm

———— 100nm

———— 100nm

DRUG CARRIERS

This is a continuation in part of U.S. Ser. No. 902,521 filed Jun. 22, 1992, now abandoned, and Ser. No. 898,168 filed Jun. 12, 1992, now abandoned. Ser. No. 902,521 is a continuation of U.S. Ser. No. 516,427 filed Apr. 30, 1990 (now abandoned) which is a continuation in part of our application Ser. No. 262,431 filed Oct. 25, 1988 (now abandoned). Ser. No. 898,168 is also a continuation of Ser. No. 262,431 (now abandoned).

This invention relates to an improved drug carrier in the form of a fatty emulsion which improves the delivery of a drug contained therein from the bloodstream or an applied site into lesional tissue.

BACKGROUND OF THE INVENTION

Various investigations have been hitherto made on drug carriers for improving delivery of a drug contained therein from the bloodstream or an applied site to a lesional tissue. For example, a method is known for utilizing liposome prepared with a phospholipid incorporated therein ("Drug Carriers in Biology and Medicine" (1979), Ed. by G. Gregoriadis, Academic Press).

According to this method, however, defects are encountered in that there are problems in the stability of liposomes enveloping an aqueous phase with a lipid bilayer during its storage and in the case of administration into blood, almost all liposomes are taken up into tissue with a developed reticuloendothelial system (RES) such as liver, spleen, etc. so that they are difficult to distribute to other cells or tissues, etc. This is believed to be the case since liposomes have a structure wherein the inner and outer aqueous phases are separated from each other by a phospholipid bilayer and the liposome is thus unstable to various forces. An increase in particle diameter due to aggregation is another known defect during its storage.

According to investigations in recent years, a technique is known in which various drugs are dissolved in a fat or fatty emulsion having a particle diameter of 0.2 μm and composed of soybean oil and yolk lecithin heretofore used clinically as a fluid supplementation for purposes of nutrient supplements when the solution is used and good results are thereby obtained according to the invention as described above (SAISHIN SGAKU (Latest Medicine), 40, 1806–1813 (1980). This carrier is characterized in that it has no internal aqueous phase and can be extremely well stored with stability as compared to liposomes.

However, the carrier of the invention has a property that is readily and rapidly taken up into the aforesaid reticuloendothelial system such as the liver, etc. Such a rapid metabolism is desired as a calorie fluid supplementation but involved problems of causing poor distribution of a drug into other tissues as a drug carrier adapted for the object described above, etc. and was not necessarily desirable.

Further, the concept of using fat or a fatty emulsion whereof 90% is 100±30 nm as a carrier for pharmaceuticals is disclosed in Japanese Laid Open Application 63/500456. However, preferential accumulation on the reticuloendothelial system such as liver and spleen occurs and, as already described, raises a problem in the delivery of a drug to other tissues.

It is most important in the transfer of drugs to the infection focus in other parts of the body that the drug carrier avoid incorporation into the reticuloendothelial system. Development of just such drug carriers having this property have been awaited. In particles having a size distribution of 100±30 nm, it is apparent that most of the drugs therein are present in sizes not less than 100 nm. This can be easily calculated by the fact that the volume of a particle is proportional to the cube of its diameter and it shows that drugs existing in particles are mostly distributed to the side of particles of bigger size. This results in substantial transfer to the liver (i.e. reticuloendothelial system) causing the above-mentioned disadvantage.

As a means for solving the foregoing problems, a technique of applying serum lipoproteins composed of a simple lipid (including sterols, as described in the present specification), a complex lipid and an apolipoprotein as a drug carrier is known (Japanese Patent Application Laid Open No. 60-163824). However, the purpose of this carrier is to introduce a drug into cells by physiological and specific recognition of the lipoprotein. Therefore, the carrier is rapidly transferred into the tissue via its receptor so that disappearance from the blood is relatively rapid. For this reason, transfer into a tissue having a poor receptor activity is not always sufficient. Furthermore, an apolipoprotein is indispensable as a constituent so that the technique is subject to a defect in industrial technique that results in high production costs.

Further, all attempts to make a fat emulsion of 200 nm particle size more fine is known (cf. Japanese Laid Open No. 62/29511). However, in this art, yolk lecithin is infrequently used and, accordingly, the resulting microparticles are recoagulated only after a time lapse resulting in a problem of instability. Moreover, there is a disadvantage with respect to the stability in vivo, so this procedure is not desirable in terms of successful delivery of active therapeutic agents to other tissues.

The present invention provides for a composition useful for improved drug delivery upon administration, which comprises a core comprising a lipophilic substance and a surface covering for the core, wherein one of the core or a part thereof or the surface covering or a part thereof comprises the drug to be administered and the other comprises a carrier therefor, the carrier having a particle diameter not less than 10 nm up to 100 nm and wherein the carrier is selected from the group consisting of compound lipids, simple lipids and derived lipids and the drug is present per se or in the form of a lipid mixture, the composition comprising 30% to 65% core and 35% to 70% surface covering.

A curve connected with ● and a curve connected with ○ represent the test sample and the comparative sample, respectively.

Figure 7:
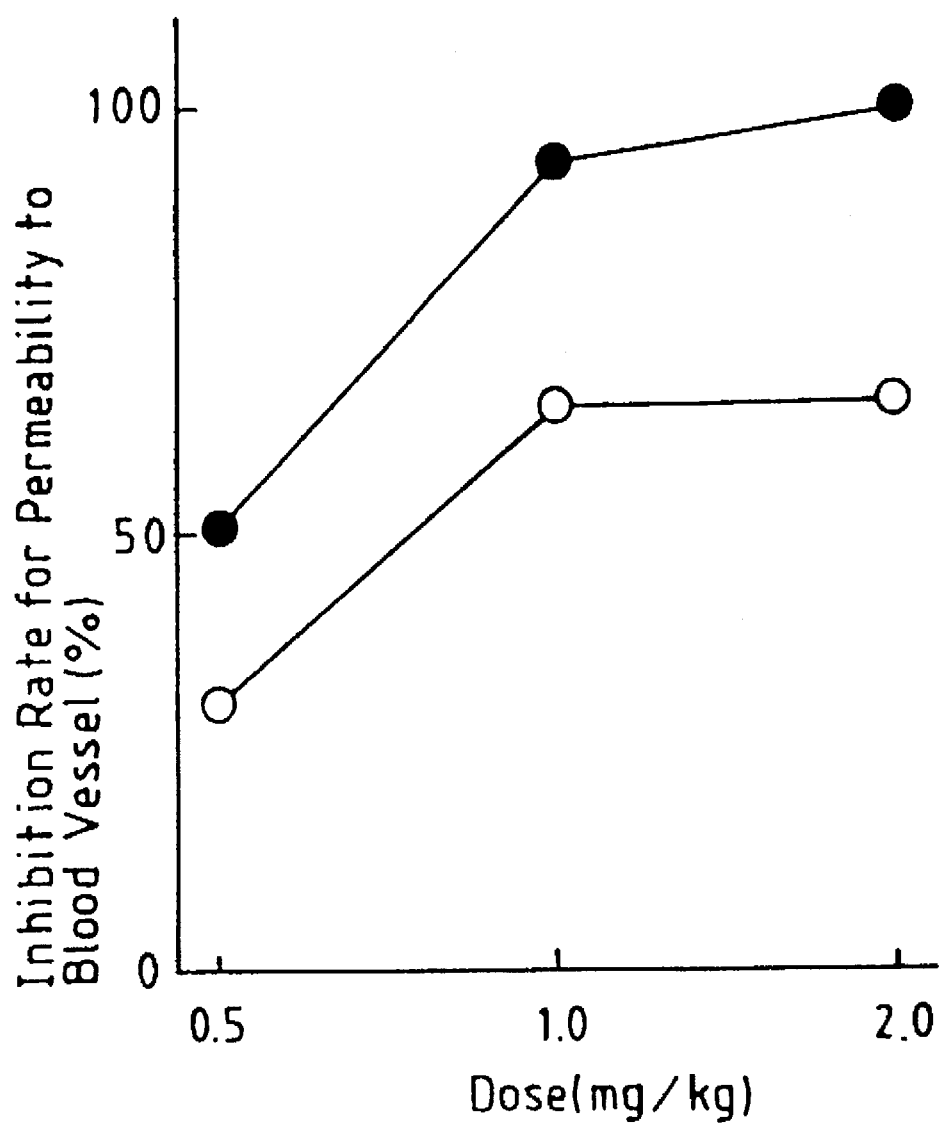

FIG. 7 represents a dose-response curve in inhibition of the vasopermeability when the test sample and the comparative sample examined in Test Example 2-12 were intravenously administered to rats, wherein the vertical axis represents the inhibition of the vasopermeability by percent and the abscissa represents the dose of the drug calculated as Diphenhydramine hydrochloride on a logarithmic scale.

A curve connection with ● and a curve connected with ○ represent the test sample and the comparative sample, respectively.

Figure 8:
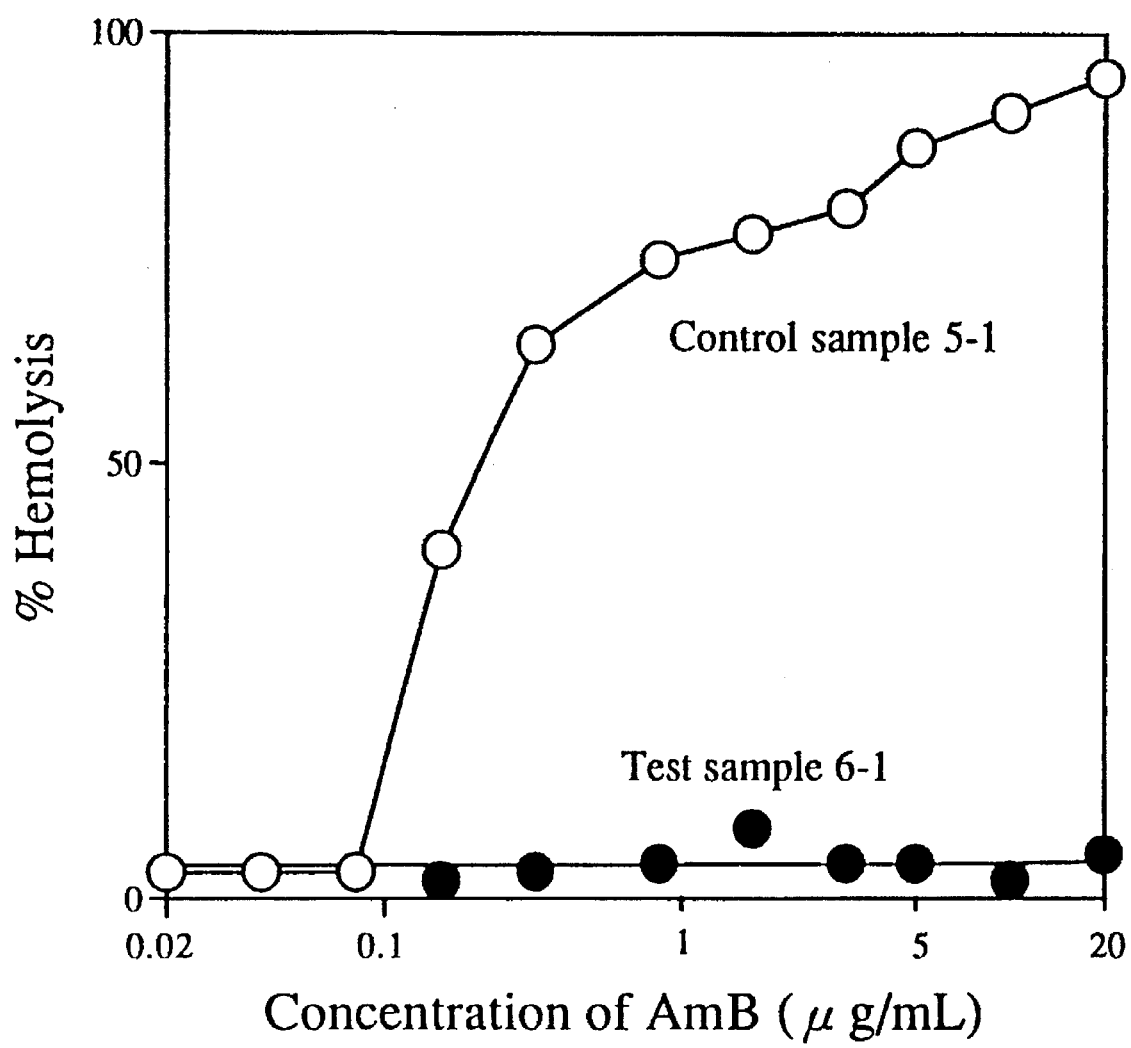

FIG. 8 is a diagrammatic representation of the results of an in vitro hemolysis assay using rat erythrocytes for Test Sample 4-1 and Control Sample 5-1. The abscissa represents the concentration of amphotericin B and the ordinate represents hemolysis. The mark ● denotes Test Sample 6-1 and the mark ○ denotes Control Sample 5-1.

Figure 9:
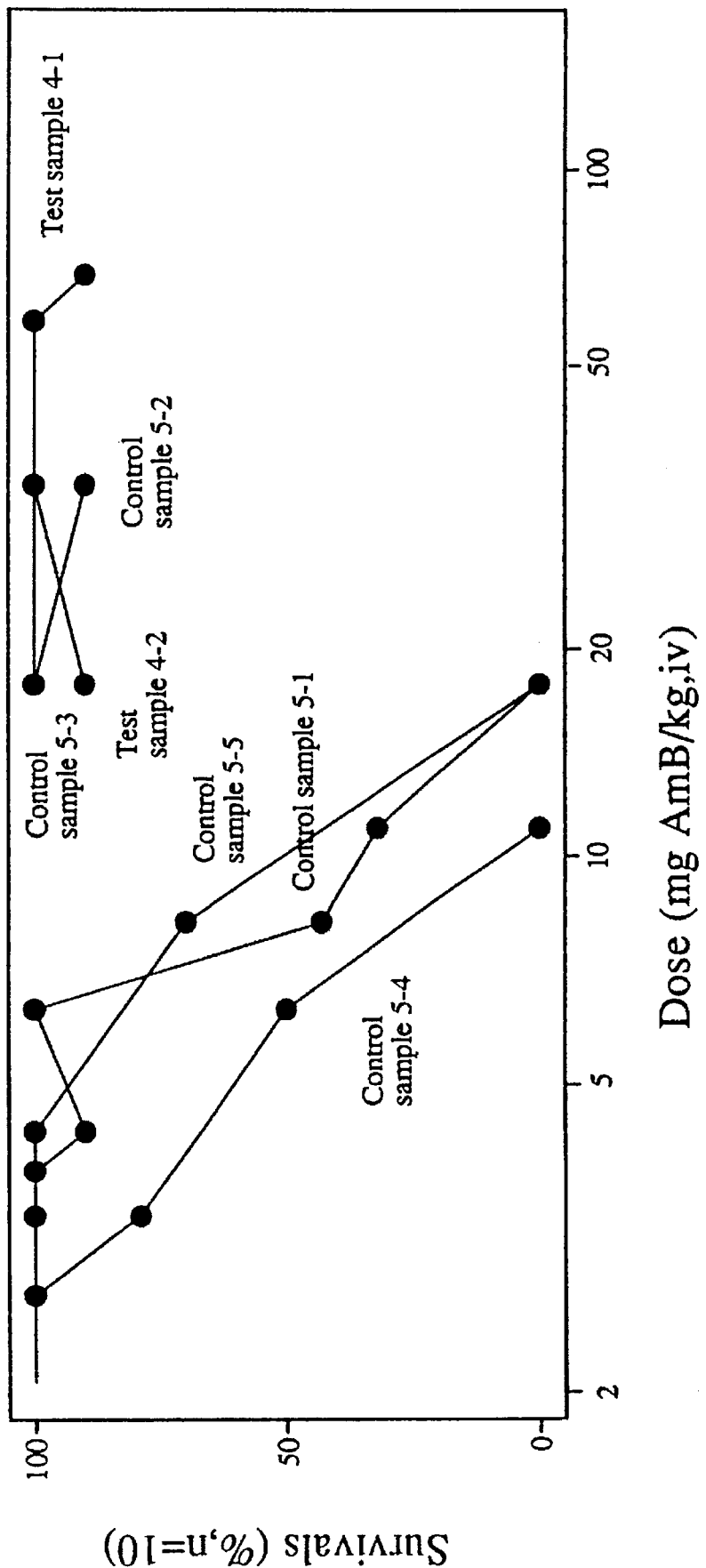

FIG. 9 is a diagrammatic representation of the results of a toxicity evaluation based on the survival rates of mice at 1 hour after administration of test and control samples to mice. The abscissa represents the dose as amphotericin B and the ordinate represents the survival rate of mice at 1 hour after administration. The line interconnecting the plots is identifiable from the designation of the corresponding sample.

Figure 10:
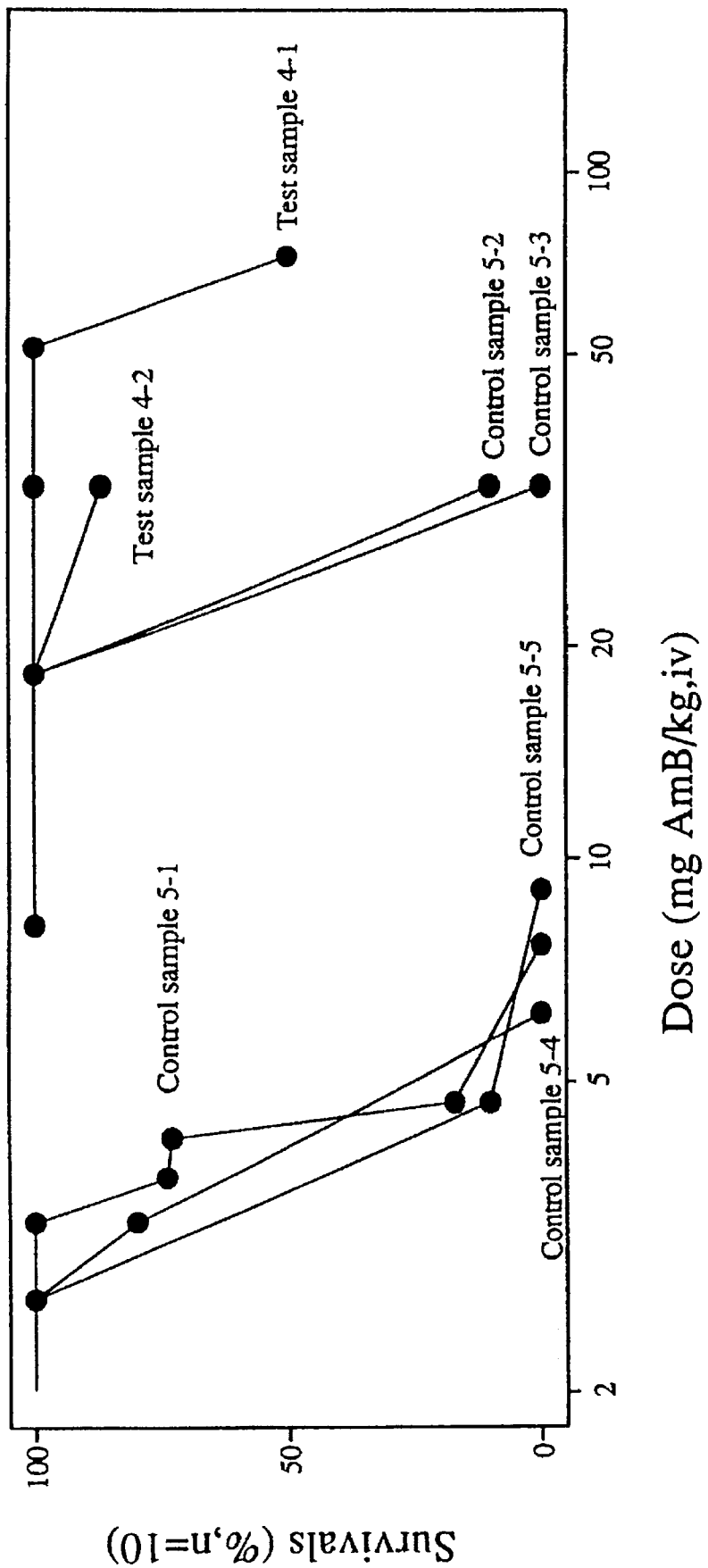

FIG. 10 is a diagrammatic representation of the results of a toxicity evauulation based on the survival rates of mice at 72 hours after administration of test and control samples. The abscissa represents the dose of amphotericin B and the ordinate represents the survival rate of mice after 72 hours. The line interconnecting the plots is identifiable from the designation of the corresponding sample.

Figure 11:
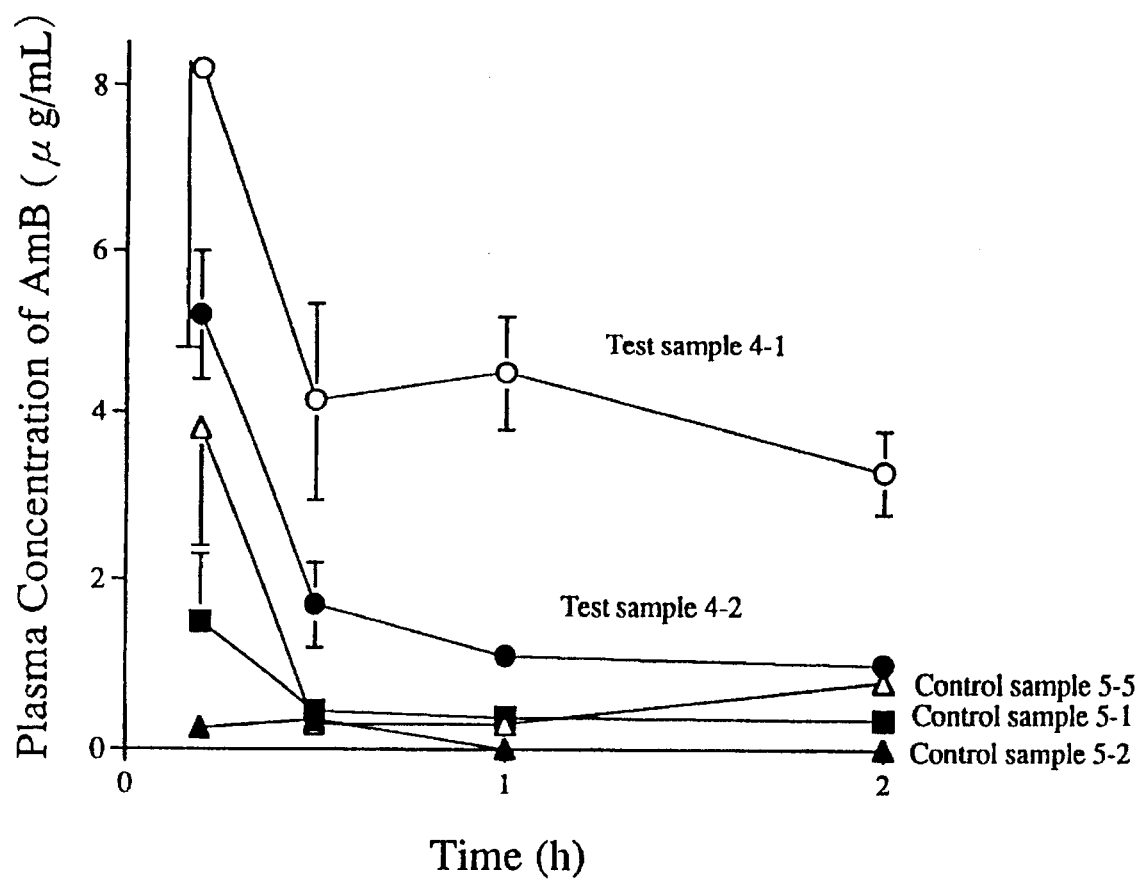

FIG. 11 is a time-course chart of the concentration of amphotericin B in the plasma after administration of each test or control sample. The abscissa represents the time after administration and the ordinate represents the plasma concentration of amphotericin B. The line indicated by the mark ○ corresponds to Test Sample 6-1, the line indicated by the mark ● corresponds to Test Sample 6-2, the line indicated by the mark ■ corresponds to Control Sample 5-1, the line indicated by the mark ▲ corresponds to Control Sample 5-2, and the line indicated by the mark △ corresponds to Control Sample 5-5.

Figure 12:
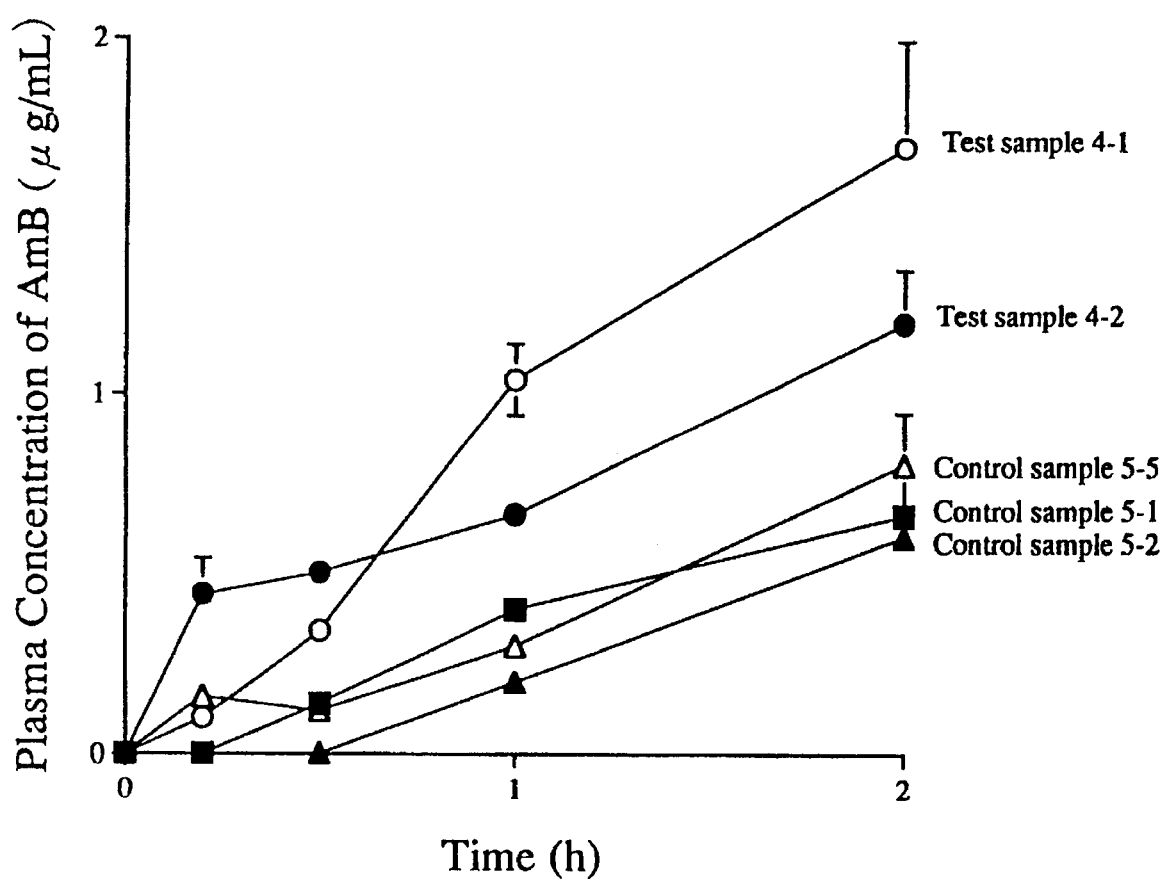

FIG. 12 is a time-course chart of the concentration of amphotericin B in pleural exudate after administration of each test or control sample to rats with experimental pleurisy. The abscissa represents the time after administration and the ordinate represents the concentration of amphotericin B in pleural exudate. The line indicated by the mark ○ corresponds to Test Sample 6-1, the line indicated by the mark ● corresponds to Test Sample 6-2, the line indicated by the mark ▲ corresponds to Control Sample 5-1, the line indicated by the marks corresponds to Control Sample 5-2, and the line indicated by the mark △, corresponds to Control Sample 5-5.

Figure 13:
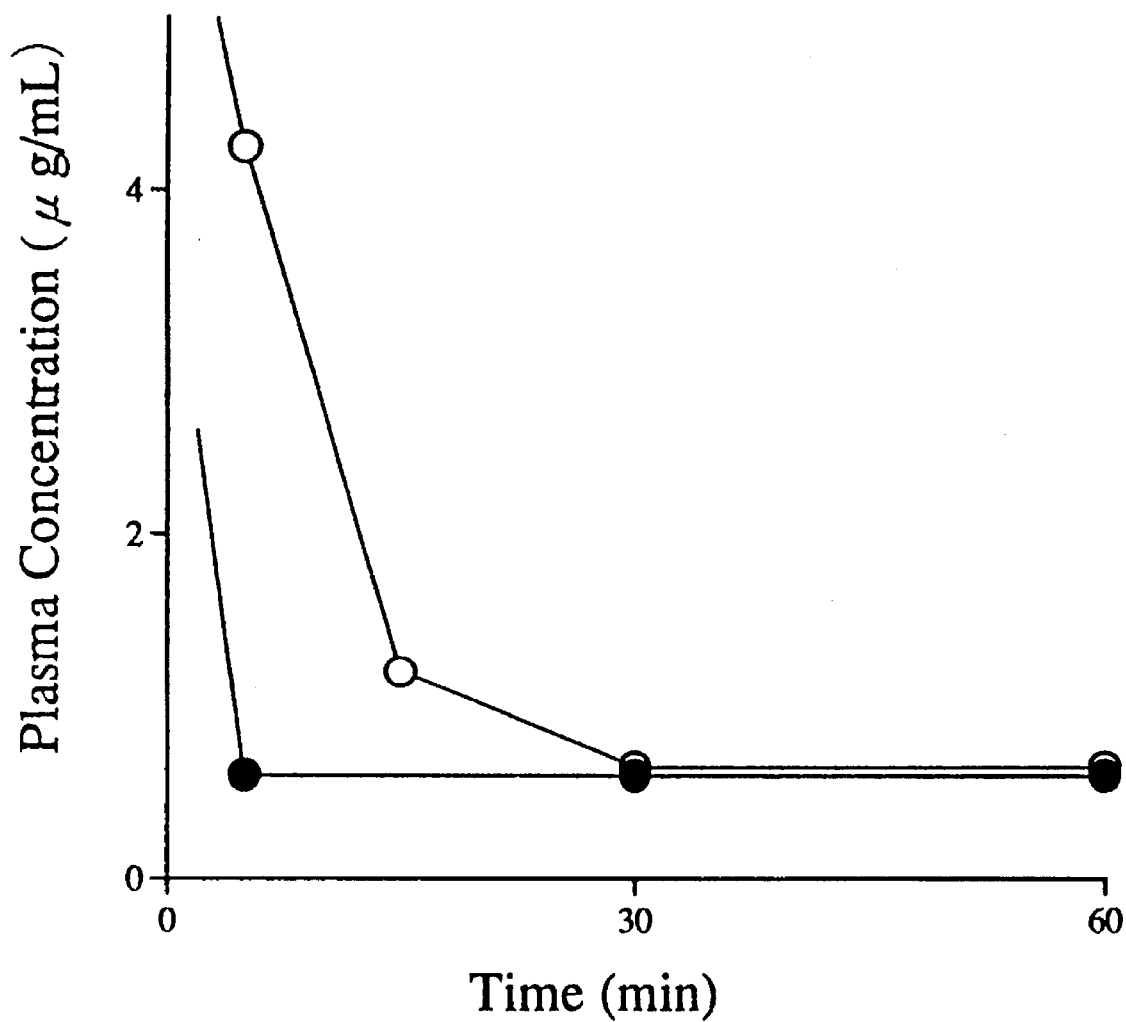

FIG. 13 shows the results of Test Example 8-1, wherein the vertical axis indicates concentration (μg/ml) of the drug in plasma and the abscissa indicates a time period (minute) after administration; ● and ○ show the comparative sample and the test sample, respectively.

Figure 14:
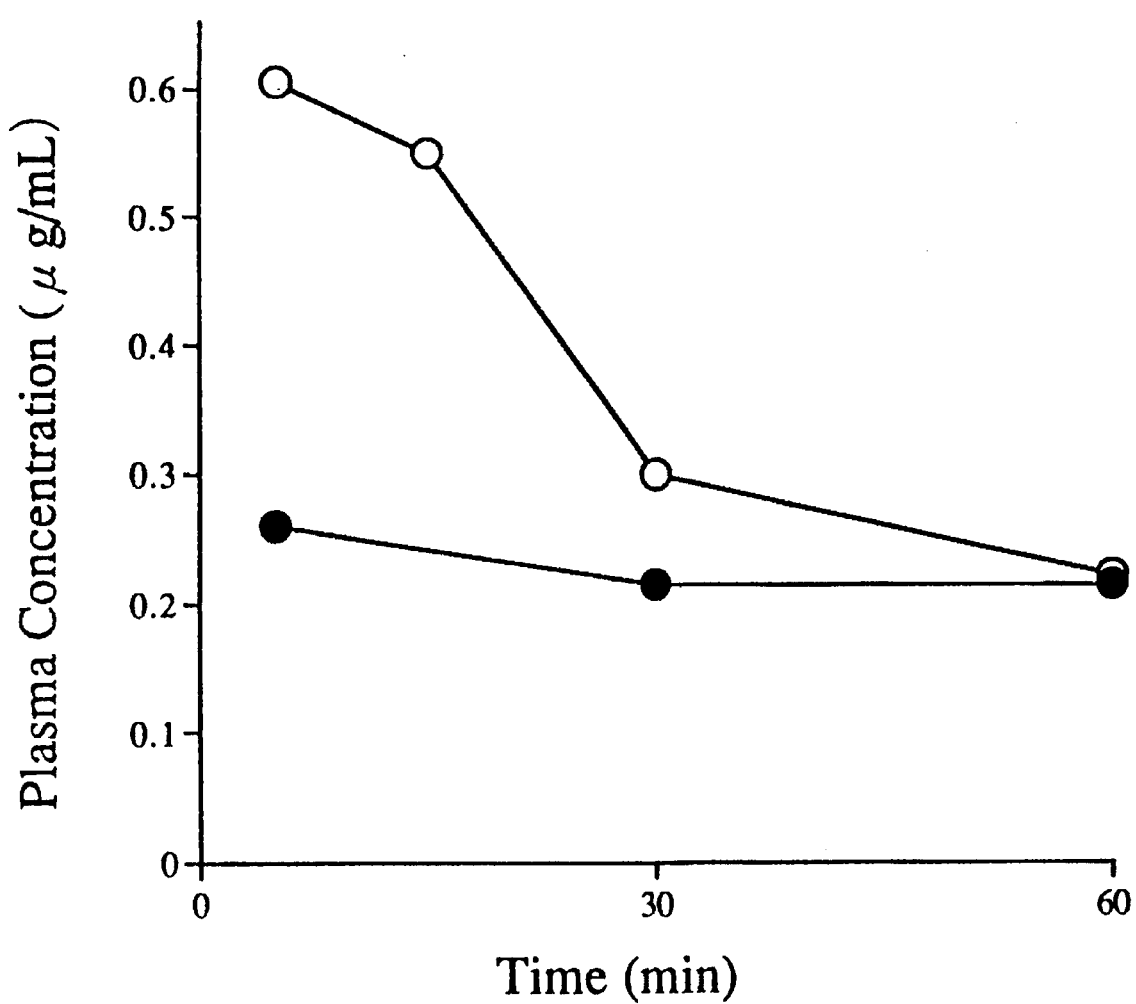

FIG. 14 shows the results of Test Example 8-2 wherein the vertical axis indicates concentration (μg/ml) of the drug in the fluid exuded into the thoracic cavity plasma and the abscissa indicates a time period (minute) after administration; ● and ○ show the comparative sample and the test sample, respectively.

Figure 15:
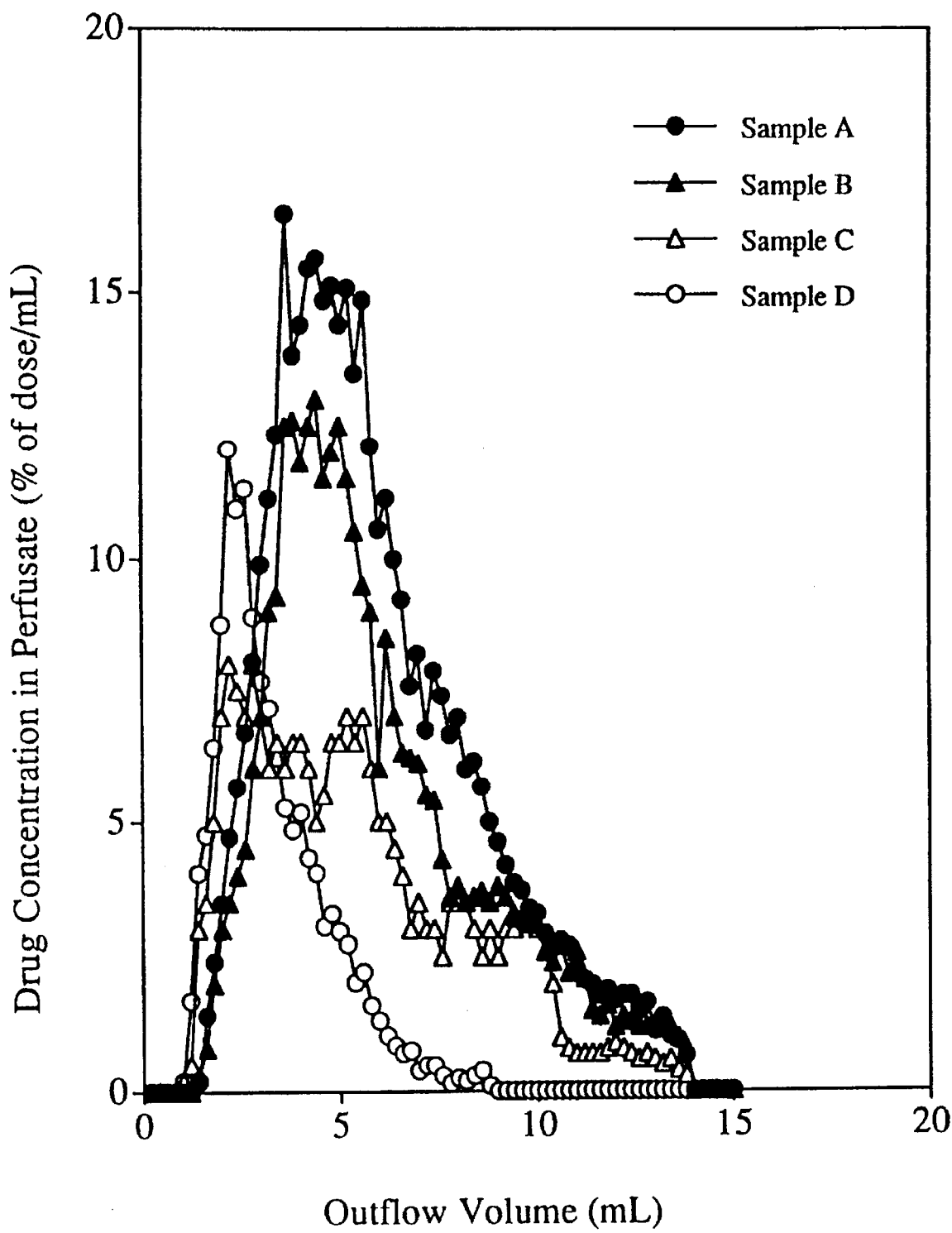
Figure 17A:
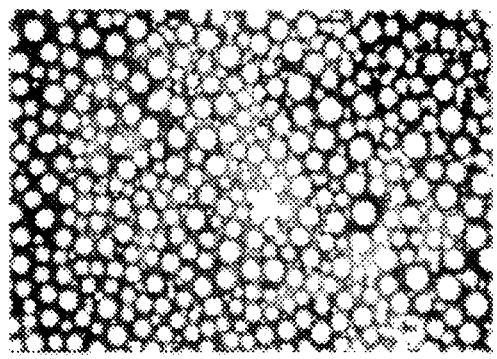
Figure 17B:
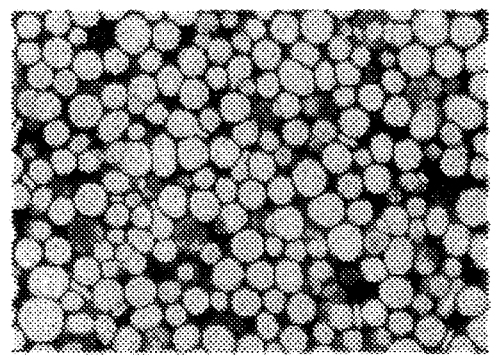
Figure 17C:
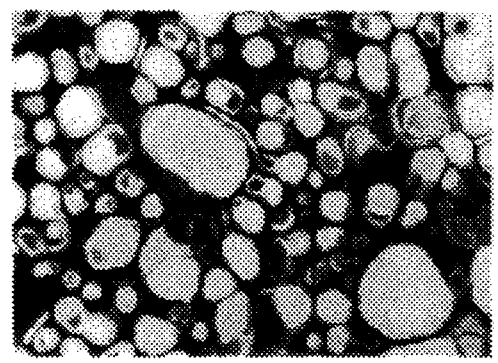
Figure 17D:
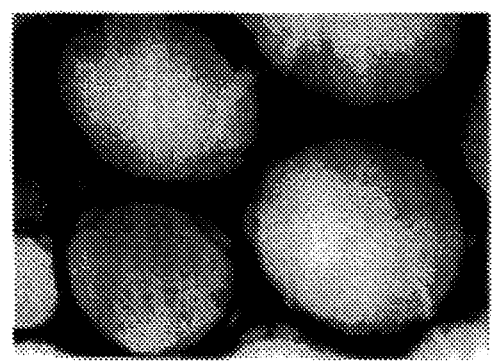

FIGS. 15–16 show the results of a single-pass liver perfusion of LNS in rats.

Male Sprague-Dawley rats (Ca. 250 g) were used in the liver perfusion test. Perfusion of the rat liver was carried out using the conventional method as described below. The rats were anesthetized by intraperitoneal injection of sodium pentobarbital (50 mg/kg), the abdomen and chest were opened, and the portal vein and the inferior vena cava were cannulated with a polyethylene tubing (PE-160). Diluted rat whole blood with Krebs-Ringer bicarbonate buffer containing small amount of heparin, pH 7.4 (1:1, v/v) was aerated with 95% $O_2$:5% $CO_2$ and pumped at 37° C. into the cannulate portal vein with the aid of a peristaltic pump at a rate of 8 mL/min. Ten minutes after the start of perfusion, 0.2 mL of the preparation containing 16 μg of dexamethasone palmitate (Sample A, B and D) or 0.4 mg of egg phosphatidyl choline (Sample C) was rapidly injected at the portal vein side. Immediately after injection, the outflow from vena cava was collected into weighed test tubes in fractions of 3 drops each. The sample volume was calculated from the gain in weight of the tube. The sample was subjected to assay for determination of the recovery from the liver. The recovery means percent of the drug recovered from the liver outflow to the injected amount into the liver.

A detailed description of samples tested in the liver perfusion test in FIGS. 15 and 16 is as follows:

Sample A: Example 5 in this specification of this invention

Sample B: Example 4 in this specification of this invention

Sample C: Example 1 in Vigne's specification (PCT/US86/01035) completely traced in their preparation and fractionation procedures. The mean diameter was about 80 nm with wide distribution in size.

Sample D: The comparative sample in Test Example 2-1 in this specification.

FIG. 17 shows an electron micrograph of the samples with negative stain technique. Samples A and B are samples of the present invention; sample C is a sample from Vigne's specification (PCT/US86/01035); and sample D is conventional fat emulsion for intravenous nutrition.

DETAILS OF THE INVENTION

In general, an administered drug moves and is distributed in the body due to properties inherently possessed by the drug molecule and when the drug reaches the site of action it exhibits its pharmacological effects. Preferably, it is desired that the drug is concentrated only on the site necessary for exhibiting the pharmacological effects but usually the drug is widely distributed throughout the entire body and to sites that do not require the drug. This sometimes become a cause for undesirable side effects and thus it becomes important and necessary to improve disposition of a drug in the body.

In view of the circumstances described above, the present inventors have continued to investigate novel drug carriers, (1) without affecting pharmacological activities per se of a drug, (2) capable of effective delivery of a drug into focal tissue, (3) capable of reducing uptake by the reticuloendothelial system, (4) capable of maintaining an effective concentration of a drug in the blood, and (5) capable of reducing the dosage drug required. These results have been achieved by the present invention.

The present invention is characterized as follows:

(1) The drug carrier is a fat or fatty emulsion constituted by both a lipophilic substance as the core and a lipophilic substance as the surface layer thereof and is not in the form of a liposome with an internal aqueous phase;

(2) In the drug carrier, a drug is present in a state of dispersion, dissolution, formation of mixed micelles or chemical binding with lipid; and (3) The particle diameter is in a range of not less than 5 to less than 100 nm or, preferably, from not less than 5 to 70 nm, in order to avoid uptake into the reticuloendothelial system.

In another embodiment a mean particle diameter of 10 to 70 nm especially 15 to 50 nm is preferred, the distribution is a log-normal distribution and the coefficient of variation is less than 100%.

The "coefficient of variation" is well known as "CV value" which is derived from the equation:

$$CV = \frac{SD}{\text{mean}} \times 100$$

See, e.g., Miller et al, Probability and Statistics For Engineers, 2d Ed., pg. 1–43, Prentice-Hall, New Jersey, 1977.

By super finely dividing the drug carrier, its blood concentration can be maintained at a higher level than that in a fat or fatty emulsion having a diameter of about 0.2 μm. Particularly preferred is mean particle diameter of 70 nm or somewhat less. This is because the drug carrier can easily exude out of a blood vessel through a region in which vasopermeability is accentuated.

The present invention comprises a composition useful for improved drug delivery wherein uptake of the drug into the liver is less than 50% when the uptake is determined by the single-pass liver perfusion method, which comprises a fatty emulsion of particles which is not in the form of a liposome wherein the emulsion of particles comprises particles having a diameter of not less than 5 to less than 100 nm, and preferably 90% of the particles have diameters smaller than 70 nm, each particle comprises a core and a surface layer wherein the substance constituting the core is a simple lipid and the core forms 30% to 85%, preferably 30% to 65%, w/w of the particle, the substance constituting the surface layer is different from that comprising the core and is a compound lipid, the surface layer forms 15% to 75%, preferably 35% to 70%, w/w of the particle and wherein the composition contains a therapeutically effective amount of a therapeutic agent, the agent being in the core, the surface layer or both.

According to a further embodiment of the present invention, the particles have a mean particle diameter of from about 16 nm to about 48 nm.

According to a further embodiment, the present invention comprises a composition useful for improved drug delivery wherein uptake by the liver is less than 40% when the uptake is determined by the single-pass liver perfusion method, which comprises a fatty emulsion of particles which is not in the form of a liposome wherein the emulsion of particles comprises particles having a mean particle diameter of 15 to 70 nm and 90% of the particles have diameters smaller than 70 nm, each particle comprises a core and a surface layer wherein the substance constituting the core is a simple lipid and the core forms 30% to 65% w/w/ of the particle, the substance constituting the surface layer is different from that comprising the core and is a compound lipid, the surface layer forms 35% to 70% w/w/of the particle and wherein the composition contains a therapeutically effective amount of a therapeutic agent, the agent being in the core, the surface layer or both.

This invention includes also a composition useful for improved drug delivery wherein transfer or uptake of drug into the liver at 30 minutes after injection is about 7.71/17.84(=0.43) when compared in case of conventional fat emulsion having a diameter of 0.2 μm, which comprises a fatty emulsion of particles which is not in the form of a liposome wherein the emulsion of particles comprises particles having a diameter of not less than 5 to less than 100 nm, and 90% of the particles have diameters smaller than 70 nm, each particle comprises a core and a surface layer wherein the substance constituting the core is a simple lipid and the core forms 30% to 85% w/w of the particle, the substance constituting the surface layer is different from that comprising the core and is a compound lipid, the surface layer forms 15% to 75% w/w of the particle and wherein the composition contains a therapeutically effective amount of a therapeutic agent, the agent being in the core, the surface layer or both.

It is known that various regions called pore systems (it is said that a small pore system having a diameter up to 9 nm and a large pore system having a diameter of 25 to 70 nm are present and it is known that the vasopermeability is further increased in various focal regions including neoblastic vessels) or other slits between cells are present in blood vessels and vasopermeability is accentuated in various focal regions including inflammation, tumor and atherosclerosis. In such a region, the drug carrier of the present invention is selectively exuded from the blood vessels in large amounts and transferred into focal tissue. At the same time, the drug contained in the drug carrier is also delivered into the body lesion. By this means, the drug can easily be delivered to the focal region selectively so that the drug concentration at the focal region increases and its effect can be enhanced. Further, by applying the principles of the drug carrier of the present invention, a drug can be administered simultaneously with a lipid so that sustained releasability of a drug and lymphotropic properties of a drug can be improved. The drug carrier of the present invention also subjects the phagocytable properties to phagocytosis.

A characteristic feature of the present invention lies in using super finely divided lipids as a drug carrier. By means of the super finely divided particles, the problems described above are solved and not only are the foregoing disadvantages not exhibited but also uptake by the reticuloendothelial system is prevented, etc. Accordingly the effect of maintaining the drug concentration in the blood can also be obtained.

The drug carrier in accordance with the present invention is further characterized in that by using larger amounts of the surface layer (for example, compound lipid) in proportion to the core (for example, simple lipid) as compared to the conventional high caloric fluid supplementation, comprising soybean oil and yolk lecithin, super finely divided particles are obtained.

In order to facilitate super finely divided particles in the drug carrier of the present invention, it is desired that the content of the surface layer (for example, compound lipid) be in a range of 35% to 70%. This is because a surface area of the core in the drug carrier is increased by super fine division, so that it is necessary to increase an amount of the compound lipid in order to cover the core as a surface layer and to stabilize the emulsion. In the case of using less than 35% of compound lipid, it is unavoidable to intermingle particles having a diameter of 0.2 µm or more while using more than 70% of compound lipid, it is unavoidable to intermingle liposome particles. By this compositional constitution, a stable emulsion of super finely divided lipid emulsion can be obtained which is usable as an extremely excellent drug carrier has been obtained for the first time.

That is, it is considered that the drug carrier of the present invention would be in the form of a fat or fatty emulsion composed of a substance as the core and a substance as the surface layer, wherein (1) the substance constituting the core of the emulsion is a simple lipid, a lipid derivative, a drug itself or a mixture thereof and the range of said substance in the drug carrier is 30 to 65%; (2) the substance constituting the surface layer of the fat emulsion is a compound lipid, a derived lipid, a drug itself or a mixture thereof and the range of said substance in the drug carrier is 35 to 70%; and by possessing properties (1) and (2) at the same time, the drug carrier containing a drug therein having a mean particle diameter of 100 nm or less, preferably 10 to 70 nm and especially not less than 5 to 70 nm, particularly 15 to 70 nm, and 15 to 50 nm can be obtained.

In the present invention, it is required that the manner of containing the drug should be dispersing or dissolving in the drug carrier, forming a mixed micelle with a constituent(s) of the drug carrier or chemically binding with a constituent (s) of the drug carrier so that the applied drug is not readily released from the drug carrier.

As the lipid used in the drug carrier of the present invention, mention may be made of a simple lipid, derived lipid or a compound lipid derived from natural animal, vegetable or mineral matter or a mixture thereof. Examples include a simple lipid, a lipid derivative or a complex lipid derived from yolk, soybean, cotton, linseed, corn, sesame, peanut, safflower, bovine tissue, hog tissue, sheep tissue, etc. as a simple lipid, a derived lipid or a compound lipid wholly synthetically prepared.

Examples of the simple lipid include neutral lipids such as refined soybean oil, cotton seed oil, linseed oil, sesame oil, corn oil, peanut oil, safflower oil, triolein, trilinolein, tripalmitin, tristearin, trimyristin, triarachidonin, etc. In general, however, the above-given commercially-available plant oil obtained from nature contains a lot of impurities and, accordingly, it is not preferred for the manufacture of the drug carrier of the present invention and also in terms of stability. Thus, it is preferred to use highly purified oil by conventional means such as steam distillation and vacuum distillation. The simple lipid also embraces cholesterol derivatives such as cholesteryl oleate, cholesteryl linoleate, cholesteryl myristate, cholesteryl palmitate, cholesteryl arachidonate, etc. This is because neutral lipids are relatively easily decomposed by various lipases present in blood vessel endothelium, etc., whereas cholesterol derivatives are decomposed only with difficulty by these enzymes.

As derived lipids there are included cholesterol, fatty acids such as stearic acid, palmitic acid, oleic acid, linoleic acid, linolenic acid, eicosapentaenoic acid, etc. and derivatives thereof, squalene, etc. They may also be used as emulsification aids. Furthermore, oily compounds such as azone, etc. may be exemplified.

As the complex lipid, mention may be made of, for example, phospholipids derived from yolk, soybean, bovine tissue, hog tissue, etc. or phospholipids and glycolipids wholly synthetically produced. Examples of phospholipids include phosphatidyl choline, phosphatidyl ethanolamine, phosphatidyl serine, phosphatidyl inositol, etc., which are exemplified by yolk phosphatidyl choline, soybean phosphatidyl choline, dipalmitoyl phosphatidyl choline, dimyristoyl phosphatidyl choline, distearoyl phosphatidyl choline, dioleoyl phosphatidyl choline, dipalmitoyl phosphatidyl inositol, etc. Products obtained by hydrogenation of these phospholipids may also be used. Among them, a representative preferred example is yolk phosphatidyl choline. The glycolipid cerebroside, etc. Steryl glucosides, e.g., β-sitosteryl-β-D-glucoside, etc. can also be exemplified. Furthermore, lipids having a charge such as stearyl amine, dicetyl phosphate, phosphatidic acid, etc. may also be used to impart a surface charge to the drug carrier.

The drug to which the present invention is applicable may be any drug so long as it is pharmaceutically acceptable. Even a drug that is insoluble or sparingly soluble can be used. In the present invention, the drug readily forms a complex with the carrier.

In a water-soluble drug, the drug carrier of the present invention can be formed by using the drug chemically bound to the constituents (for example, lipid, etc.) of the carrier.

Even though a drug is unstable in the human body and is thus incapable of administration so far, such a drug can be readily administered by using the drug carrier of the present invention. The drug contained in the drug carrier of the present invention is present in oil droplets of lipids in a state shielded from the surrounding environment so that enzymatic or non-enzymatic decomposition can be prevented.

The drug to which the drug carrier of the present invention is applicable is not particularly limited, as described above. Examples include an anti-inflammatory agent, an analgesic, an anti-allergic agent, an antibiotic, a chemotherapeutic agent, and anti-cancer agent, antiviral agent, antiatherosclerosis, and anti-lipemic agent, an antiulcer agent, an immunoregulator, a vaccine, a radical scavenger, a bronchodilator, a hypnotic, a tranquilizer, a topical anesthetic, a diagnostic agent, etc. Specific examples of these drugs are anti-cancer agents such as ancitabine, fluorouracil, mitomycin C, mitomycin C farnesylamide, mitomycin C farnesylacetic amide, camofur, futraful palmirate, 5-fluorouracil myristate, adriamycin, Daunomycin, Aclarubicin, Maclarubicin, Vinblastine, Vincristine, Cytarabine fatty acid esters, Mitotane, Estramustine, etc.; antiviral agents such as Dichloroflavan, etc.; and steroidal agents such as Dexamethasone palmitate, hydrocortisone palmitate, Prednisolone palmitate, Dexamethasone stearate, Methylprednisolone, Paramethasone, Fluocinolone acetonide, Vectamethasone propionate, Hydrocortisone fatty acid esters, Aldosterone, Spironolactone, etc. and non-steroidal agents such as Ibuprofen, Flufenamic acid, Ketoprofen, Phenacetin, Antipyrine, Aminopyrine, Phenylbutazone indoleacetate, Biphenylylpropionic acid derivatives, Indomethacin, Indomethacin ethoxycarbonylmethyl ester, Indomethacin stearyl ester, sodium aurothiomalate cetyl ester, Diclofenac, acetylsalicylic acid and derivatives thereof, etc. Anti-allergic agents such as Tranylast, Ketotifen, Azelastine, etc. may also be used. As antibiotics and chemotherapeutic agents examples are tetracyclines, Erythromycin, Midecamycin, Amphotericin, Nalidixic acid, Griseofluvin, Minocyclin, etc. As examples of prostaglandines, there may be used PGE1, PGA1, alkyl esters, PGE1 alkyl esters, PGE1 derivatives, PGI2 derivatives, PGD2 derivatives, etc. Antihistaminic agents such as Diphenhydramine, Orphenadirine, Chlorphenoxamine, Chlorpheniramine, Promethazine, Mecridine, Cyproheptadine, Loxatidine acetate, etc. are included. Furthermore, topical anesthetics such as Lidocaine, Benzocaine, Dantrolene, Cocaine, Tetracaine, Piperocaine, Mepyracaine, and derivatives thereof, etc. are included. There are also included hepatic disorder improving agents such as Marotirate, Glycyrretinic acid, ethyl acetylglycyrrretinate, methyl glycyrretinate, etc., antiulcer agents such as Farnesol, Geraniol, Gefarnate, Teprenone, Plaunotol, Sofarcon, etc. There are also CNS agents acting on central nerves such as Phenobarbital, Methaqualon, Heroin, Diazepam, Medazepam, Frazepam, Clotiazepam, Etizolam, Mecridine, Bucridine, Adiphenine, Methamphetamine, Imipramine, Chlorimipramine, Amitriptyline, Mianserin, Trimethadione, Phensuximide, Tetrabenzamide, Benzquinamide, Camphor, Dimorphoramine, Strychnine, Chlorpronazine, Promethazine, Prochlorperazine, Mequitazine, Triflupromazine, Levomepromazine, Difenidol, etc. and derivatives thereof. Also, cerebrovasodilators such as Cinnarizine, etc. are included. As bronchodilators, there may be Vestphyllin and other theophylline derivatives, methylephedrine, etc. Anticholinergic agents may be used such as Benztropine, Physostigmine, Atropine, Scopolamine, etc., parasympathetic blockers such as Oxyphencyclimine, Pirenzemine, Etomidrine, etc. calcium blockers such as Diltiazem, Nifedipine, Verapamil, etc. α-blockers as a Dibenzamine, Phenoxybenzamine, etc., antitussive agents such as Noscapine, Dextromethorphan, Pentoxyverine, Benproperine, etc., agents for treating prostatic hypertrophy such as Gastron, Oxendelone, etc., agents for treating glaucoma such as Pilocarpine, etc., agents acting on smooth muscle such as Sparteine, Papaverine, etc., agents for treating hyperlipemia such as Chlorfibrate, Cimfibrate, Probucol, etc. and the like are all included as drugs. In addition, there is included amino acids, vitamins, Dilazep, Ubidecarenone, Flavoxate, Cyclosporin, vaccines for influenza, etc., Dibenzthione, Diphenylpyraline, Phenovalinium, Metadione, Tofisopam, Limonen, etc.

Antioxidants are also included such as tocopherol, flavone derivatives, gallic acid derivatives, coffee acid derivatives, Goshipol, Sezamol, oxyfatty acid, camphene, Cineol, Rosmanol, Eugenols, Filozurucine, etc., catechins, lignan homologues, p-coumaric acid, sterols, terpenes, bromophenol, etc. and can form the drug carrier of the present invention as one of the constituents.

Further, guaiazulene, essential oil type crude drugs such as apricot kernel oil, fennel oil, thyme oil, terepentine oil, eucalyptus oil, palm oil, poppy seed oil, tsubaki oil, peppermint oil, clove oil, mint oil, sage oil and other components for spicy crude drugs, etc. and the like can also be included as constituent factors of the drug carrier of the present invention.

As diagnostics, there may be used a compound labeled with a radioisotope, a radioactive drug or iodated poppy oil fatty acid esters as X-ray contrast materials, etc.

The drug to which the drug carrier of the present invention is applicable is not particularly limited as described above but when viewed from characteristics possessed inherently as the drug carrier, drugs which take part in inflammation, tumor, blood vessel or immune or lymphoid system are generally desirable.

The drug concentration in the drug carrier of the present invention can be suitably varied within a range such that the content does not exceed 65% in the drug carrier, according to the biological activity of the particular drug. Further, the concentration of the drug carrier of the present invention in medical preparations obtained by using the drug carrier of the present invention can be suitably varied as desired.

Upon preparation of the drug carrier of the present invention and medical preparations involving the same, various methods for preparing emulsions as hitherto performed are applicable. For example, they can be prepared according to a method which comprises sufficiently finely dividing all constituents including a drug by means of a homogenizer of the Manton-Gaurin type, a microfluidizer, an ultrasonic wave homogenizer, etc. They can be also prepared according to a method which comprises solubilizing the constituents using a surface active agent such as bile acid, a water-soluble solvent such as ethanol, polyethylene glycol, etc. and then removing the surface activity agent or water-soluble solvent, etc. by dialysis or gel filtration, and the like.

Fatty acids or derivatives thereof, etc. may also be added as emulsification aids. Furthermore, the drug carrier and its medical preparations may also be obtained by adding a drug to a fat or fatty emulsion of average particle size of not more than 100 nm, preferably 10 to 70 nm, particularly 15 to 50 nm, when previously prepared by the aforesaid methods.

In the manufacture of the drug carrier of the present invention, as well as the pharmaceutical preparation containing the same, there is no limitation as to the concentration of the components constituting the drug carrier of the present invention. Still it is preferable to manufacture the drug carrier at a concentration of not less than 10 mg/ml whereupon the drug carriers have a smaller particle size, narrower particle size distribution range and higher uniformity. Another advantage in the drug carrier of the present invention is that it is not necessary to fractionate the part having a desired particle size after manufacture and accordingly a stable drug carrier with high uniformity having desired particle size can be very easily prepared.

The shape and particle diameter of the drug carrier of the present invention can easily be confirmed by an electron microscope, a particle diameter analyzer of light scattering type, filtration through a membrane filter, etc. As optional components for medical preparations using the drug carrier of the present invention, there may be used additives and auxiliary substances commonly used for ordinary injections, etc. Examples are an antioxidant, a preservative, a stabilizer, an isotonic agent, a buffer, etc. Required and optimum amounts of these additives, auxiliary substances or the like can be varied depending upon their purposes.

The drug carrier of the present invention obtained as described above can be sterilized by filtration or with steam under high pressure in an autoclave, if necessary, and sealed in an ampoule together with nitrogen gas. Also if necessary, the drug carrier may be freeze-dried. The freeze-dried drug carrier of the present invention can be restored by adding an appropriate reconstituting solution thereto.

The drug carrier of the present invention is generally administered intravenously to humans and animals, but if necessary, can also be administered intra-arterially, intramuscularly, subcutaneously and the like.

Furthermore, the drug carrier of the present invention can also be used as an eye drop, a nose drop, an oral agent, a suppository and the like. In this case, additives such as pharmaceutically acceptable bases, excipients and the like can be employed as optional components.

According to the present invention, a value for drug availability can be markedly enhanced. The effects of the drug carrier of the present invention can be summarized in that the prior art problems are overcome, (1) delivery of a drug into the focal lesion is improved, (2) uptake by the reticuloendothelial system is prevented, (3) a blood concentration of drug contained therein can be maintained, (4) stability during storage is ensured, (5) production costs are reduced, etc. These effects have been achieved by the present invention for the first time.

Single-pass liver perfusion method is usually used for evaluation of drug delivery to liver.

Representative reference literatures for single-pass liver perfusion method are as follows:

Kiwada et al., Chem. Pharm. Bull., 34, 1249–1256 (1986), Sato et al., J. Pharm. Sci., 78, 11–16 (1989), Kiwada et al. and Sato et al. modified surgical operational method of Mortimore et al. (Diabetes, 8, 307–314 (1959)) on the rat liver. They injected test sample which contains drug to the liver through portal vein and then recovered the drug from the vein of the liver and were able to calculate accurately the rate of recovery amount against injected amount.

We understand that there is quite a different feature between Vigne et al. and this invention. That Vigne failed to apply the pharmaceutical microemulsions which were not small enough as they planed give rise to the difference.

On the other hand, Vigne et al. disclosed in the U.S. Pat. No. 5,023,271; page 3, lines 9–12: "The particles are sufficiently small to enter the liver, which appears to play a significant role in the distribution and utilization of a number of vitamins and drug metabolites." Page 7, lines 10–11: "This size particle is sufficiently small to undergo uptake by the liver,—".

Vigne et al. also disclosed in their corresponding PCT application version: PCT International Publication Number: WO 87/01035; which is thought as revised version of U.S. Pat. No. 5,023,271; page 18, lines 19–25: "Regardless of the mode of administration, it appears that the pseudomicellar composition is attracted to the liver, and approximately half of the administered dose homes to the liver and is metabolized there.

It is obvious that Vigne et al. invented the pharmaceutical microemulsions which is sufficiently small to undergo uptake by the liver. On the other hand, we invented the pharmaceutical microemulsions with extremely reduced uptake by the liver. This is a unique and useful feature of our invention and makes our invention different from invention of Vigne et al.

These different features come from the difference of made and used pharmaceutical microemulsions by each inventors. Vigne et al. disclose at the beginning (P19, L6—in the PCT version) of examples that "The by weight percentages in the starting material . . .". Vigne et al. also disclose that "In all cases, fractions of approximately 6–10 as noted specifically in the examples were collected . . ." (P20, L4-7 in the PCT version). Furthermore, at the beginning of all examples, Vigne et al. disclose "The original mixture contained". In examples 1 and 2, Vigne disclose clearly that the gradient fractions recovered had different ratios of constituent from the original ones.

In our invention, we need not operate the differential centrifugation and get very even-sized homogenous pharmaceutical microemulsions in comparison with one of Vigne et al. as shown in the enclosed picture of the electron microscopy in FIG. 17. Sample A and B are our invention. C is one of Vigne. D is conventional fat emulsion for intravenous neutrition. We had found a similar initial component ratio with Vigne et al. but obtained even-sized pharmaceutical microemulsions. This fact came from the difference of preparing method between Vigne et al. and us.

We may often make some similar starting material which has similar size but very different material which has different structure and function from a similar component(s) of raw material. We should recognize and accept these phenomena and argue the novelty and unobviousness.

In our experiences, preparations with incomplete emulsification followed by fractionation by differential centrifugation shows small diameter with PCS particle analyzer, but it is not even-sized microemulsions with electron microscopie technique. And also, it does not show reduced uptake by the liver with single pass liver perfusion method.

There is no better means other than using the uptake by the liver when the uptake is determined by a biological evaluation, the single-pass liver perfusion method, to clarify the difference between the invention of Vigne et al. and one of Sugiyama et al. Then we claim using this unusual biological property. Single-pass liver perfusion method is the most common and objective experimental method to measure the uptake by the liver. Therefore, it is not to be new matter. The real invention should be protected by this perfusion method.

It is also a characteristic that the major constituents of the drug carrier of the present invention are therapeutically acceptable lipids conventionally used for therapy in the clinical field so that they can be used extremely safely.

Hereafter the present invention will be explained in more detail, by referring to typical examples relating to the preparation of the drug carrier of the present invention by deemed to be limited thereto.

EXAMPLE 1

To 27 mg of triolein were added 38 mg of yolk lecithin and 10 mg of guaiazulene (anti-inflammatory agent) and, 10 ml of physiological saline was added to the mixture. Using a probe type ultrasonic wave homogenizer (Branson Sonifier Model 185), the mixture was subjected to an ultrasonic wave treatment for 60 minutes under ice-cooling. The formed drug carrier containing guaiazulene was blue and clear. The mean particle diameter of the drug was 26.4 nm when measured by a light scattering particle diameter measurement device. Further in observation by an electron microscope, the drug carrier was recognized to be uniform, spherical ultra finely divided particles. Any lipid bilayer membrane as in liposome was not observed. It was also noted that the drug carrier passed by 100% through a filtering membrane of 0.2 µm and did not contain particles of 0.2 µm or more.

EXAMPLE 2

Yolk lecithin, 2.5 mg and 10 mg of guaiazulene were mixed and 10 ml of physiological saline was added to the mixture. Using a probe type ultrasonic wave homogenizer (Branson Sonifier Model 185), the mixture was subjected to ultrasonic wave treatment for 60 minutes under ice-cooling. The formed drug carrier containing guaiazulene had a mean particle diameter of 48.4 nm according to an apparatus for measuring optical scattering particles. It was also noted that the drug carrier passed by 100% through a filtering membrane of 0.2 µm and did not contain particles of 0.2 µm or more.

EXAMPLE 3

To 100 mg of triolein were added 100 mg of yolk lecithin and 4 mg of a compound (Dexamethasone palmitate) obtained by chemically binding a fatty acid with Dexamethasone(anti-inflammatory agent) and, 10 ml of 0.24M glycerin aqueous solution was added to the mixture. Using a probe type ultrasonic wave homogenizer (Branson Sonifier Model 185), the mixture was subjected to ultrasonic wave treatment for 60 minutes under ice-cooling. The formed drug carrier containing Dexamethasone palmitate was slightly bluish white and clear. A mean particle diameter of the drug carrier was 29.9 nm when measured by a light scattering particle diameter measurement device.

It was also noted that the drug carrier passed by 100% through a filtering membrane of 0.2 µm and did not contain particles of 0.2 µm or more.

EXAMPLE 4

To 80 mg of triolein were added 20 mg of cholesteryl linoleate, 100 mg of yolk lecithin and 4 mg of Dexamethasone palmitate. Then, 10 ml of 0.24M glycerin aqueous solution was added to the mixture. Using a probe type ultrasonic wave homogenizer (Branson Sonifier Model 185), the mixture was subjected to ultrasonic wave treatment for 60 minutes under ice-cooling. The formed drug carrier containing Dexamethasone palmitate was slightly bluish white and clear. A mean particle diameter of the drug carrier was 30.6 nm when measured by a light scattering particle diameter measurement device. It was also noted that the drug carrier passed by 100% through a filtering membrane of 0.2 µm and did not contain particles of 0.2 µm or more.

EXAMPLE 5

To 100 mg of cholesteryl linolate were added 100 mg of yolk lecithin and 4 mg of Dexamethasone palmitate. Then, 10 ml of 0.24M glycerin aqueous solution was added to the mixture. Using a probe type ultrasonic wave homogenizer (Branson Sonifier Model 185), the mixture was subjected to ultrasonic wave treatment for 60 minutes under ice-cooling. The formed drug carrier containing Dexamethasone palmitate was slightly bluish white and clear. A mean particle diameter of the drug carrier was 22.7 nm when measured by a light scattering particle diameter measurement device. It was also noted that the drug carrier passed by 100% through a filtering membrane of 0.2 µm and did not contain particles of 0.2 µm or more.

EXAMPLE 6

To 100 mg of triolein were added 100 mg of yolk lecithin and 10 mg of Diphenhydramine (antihistaminic agent). Then, 10 ml of 0.24M glycerin aqueous solution was added to the mixture. Using a probe type ultrasonic wave homogenizer (Branson Sonifier Model 185), the mixture was subjected to ultrasonic wave treatment for 60 minutes under ice-cooling. The formed drug carrier containing Diphenhydramine was slightly bluish white and clear. A mean particle diameter of the drug carrier was 31.6 nm when measured by a light scattering particle diameter measurement device. It was also noted that the drug carrier passed by 100% through a filtering membrane of 0.2 µm and did not contain particles of 0.2 µm or more.

EXAMPLE 7

To 100 mg of triolein was added 100 mg of yolk lecithin. Then, 10 ml of 0.24M glycerin aqueous solution was added to the mixture. Using a probe type ultrasonic wave homogenizer (Branson Sonifier Model 185), the mixture was subjected to ultrasonic wave treatment for 60 minutes under ice-cooling. The formed drug carrier was slightly bluish white and clear. A mean particle diameter of the drug carrier was 47.2 nm when measured by a light scattering particle diameter measurement device. It was also noted that the drug carrier passed by 100% through a filtering membrane of 0.2 µm and did not contain particles of 0.2 µm or more.

A compound (Vinblastine palmitate), 500 µg, obtained by chemically binding a fatty acid with vinblastine (anticancer agent), was added to the drug carrier obtained above. The mixture was gently mixed and stirred for 6 hours to take the drug up into the drug carrier. Thereby, the drug carrier containing the drug was obtained.

A compound (5-Fluorouracil palmitate), 500 µg, obtained by chemically binding a fatty acid with 5-Fluorouracil (anticancer agent), was added to the drug carrier obtained above. The mixture was gently mixed and stirred for 6 hours to take the drug up into the drug carrier. Thereby, the drug carrier containing the drug was obtained.

A compound (Cytarabine levulinate), 500 µg, obtained by chemically binding a fatty acid with Cytarabine (anticancer agent), was added to the drug carrier obtained above. The mixture was gently mixed and stirred for 6 hours to take the drug up into the drug carrier. Thereby, the drug carrier containing the drug was obtained.

EXAMPLE 8

Figure 1:
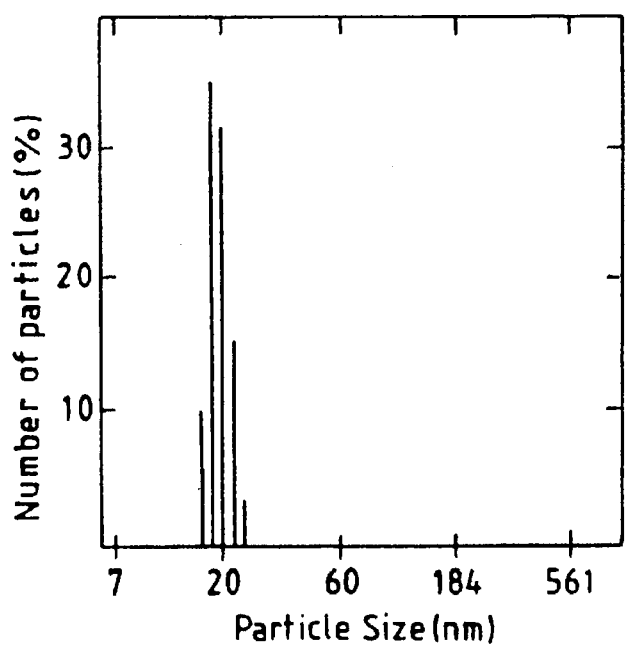
FIG. 1 shows results of a particle diameter of the drug carrier of the present invention prepared in Example 8 measured with a light scattering particle diameter measurement device, wherein the vertical axis represents the number of particles and the abscissa represents a particle diameter on a logarithmic scale.

To 80 mg of triolein were added 20 mg of cholesteryl linoleate and 100 mg of yolk lecithin. Then, 10 ml of 0.24M glycerin aqueous solution was added to the mixture. Using a probe type ultrasonic wave homogenizer (Branson Sonifier Model 185), the mixture was subjected to ultrasonic wave treatment for 60 minutes under ice cooling. The formed drug carrier was slightly bluish white and clear. A mean particle diameter of the drug carrier was 19.1 nm when measured by a light scattering particle diameter measurement device. The analytical results are shown in FIG. 1. It was also noted that the drug carrier passed by 100% through a filtering membrane of 0.2 µm and did not contain particles of 0.2 µm or more.

EXAMPLE 9

To 20 mg of refined soybean oil was added 20 mg of yolk lecithin. Then, 10 ml of 0.24M glycerin aqueous solution was added to the mixture. Using a probe type ultrasonic wave homogenizer (Branson Sonifier Model 185), the mixture was subjected to ultrasonic wave treatment for 60 minutes under ice cooling. The formed drug carrier was slightly bluish white and clear. A mean particle diameter of the drug carrier was 16.1 nm when measured by a light scattering particle diameter measurement device. It was also noted that the drug carrier passed by 100% through a filtering membrane of 0.2 μm and did not contain particles of 0.2 μm or more.

Furthermore, a drug carrier was prepared in a manner similar to above, except for using 40 mg of refined soybean oil. The formed drug carrier was slightly bluish white and clear. A mean particle diameter of the drug carrier was 37.7 nm when measured by a light scattering particle diameter measurement device. It was also noted that the drug carrier passed by 100% through a filtering membrane of 0.2 μm and did not contain particles of 0.2 μm or more.

EXAMPLE 10

To 10 g of soybean oil was added 10 g of yolk lecithin. Then, 1 liter of 0.24M glycerine aqueous solution was added to the mixture. Using a microfluidizer, the mixture was emulsified. It was noted that the formed drug carrier passed by 100% through a filtering membrane of 0.2 μm and did not contain particles of 0.2 μm or more.

TESTS ON STABILITY OF THE DRUG CARRIER OF THE PRESENT INVENTION

Test Example 1-1

The sample obtained in Example 1 was sealed in a brown ampoule of 1 ml volume together with nitrogen gas. A forced deterioration test was performed at 60° for 4 weeks in a conventional manner. The residual rate of guiazulene was 98.3% more and it was confirmed that the drug carrier of the present invention had effects on stability of the drug.

Test Example 1-2

The samples obtained in Examples 1, 3 and 4 described above were sealed, respectively, in a brown ampoule of 1 ml volume together with nitrogen gas. After a sterilizing treatment of the ampoules with steam under high pressure in an autoclave, a particle diameter of each sample was measured by a light scattering particle diameter measurement device. There was not significant difference between prior to and after the treatment. Neither aggregation nor increase in the particle diameter was noted. Further they were stored at 4° C. for 6 months without change such as aggregation, etc. being observed.

Test Example 1-3

The sample obtained in Example 3 described above was freeze-dried in a conventional manner. Thereafter, distilled water for injection was added to the sample followed by stirring to restore. Then a particle diameter of the sample was measured by a light scattering particle diameter measurement device. The mean particle diameter was 28.3 nm. There was neither significant aggregation nor increase in the particle diameter noted by the sample was uniformly dispersed.

TEST ON UTILITY OF THE PRESENT INVENTION

Test Example 2-1

The drug carrier of the present invention containing $^3$H-labeled Dexamethasone palmitate prepared in a manner similar to Example 3 was used as a test sample. As a comparative sample, a prior art fat emulsion having a diameter of 0.2 μm was used. This comparative sample was obtained by adding 10 ml of 0.24M glycerin aqueous solution to 4 mg of $^3$H-labeled Dexamethasone palmitate, 100 mg of refined soybean oil and 12 mg of yolk lecithin.

The test sample and the comparative sample were intravenously administered to rats. Thereupon, any change in blood concentration was examined.

Figure 2:
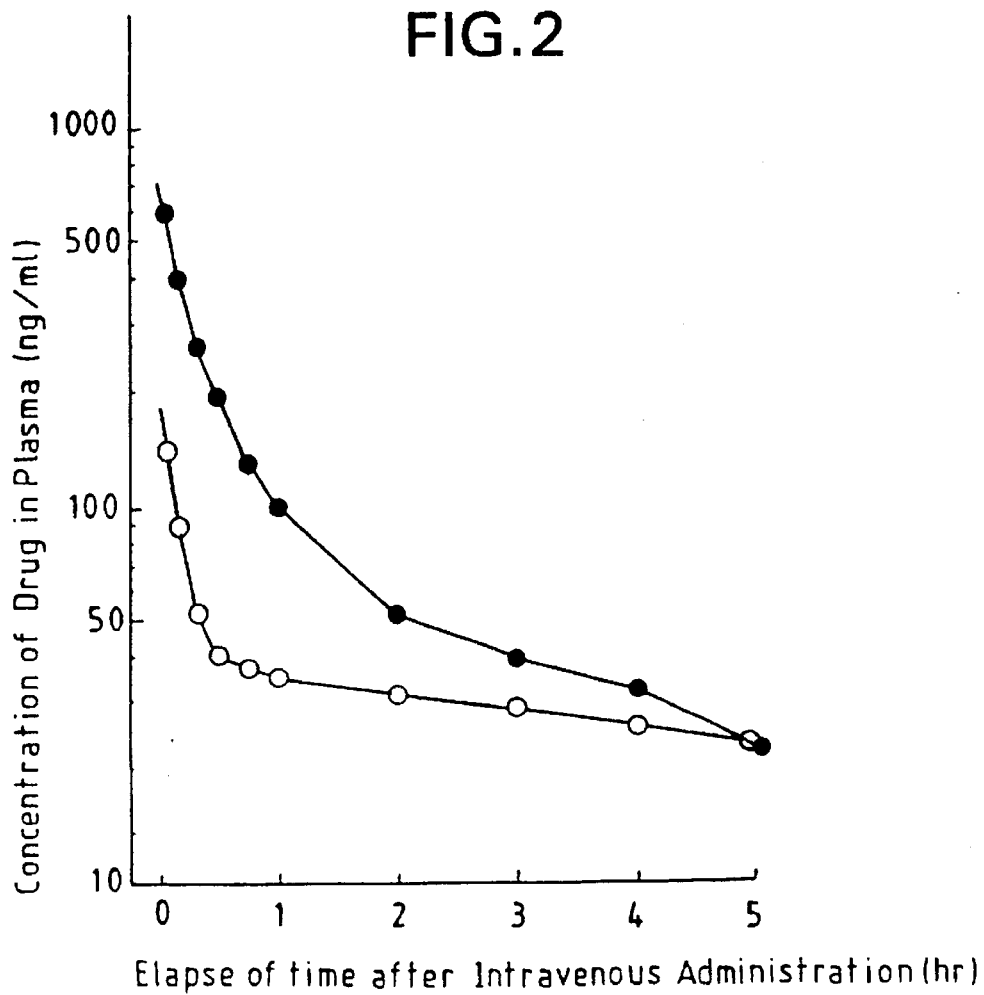
FIG. 2 shows change of the total radioactivity in plasma when the test sample and the comparative sample examined in Test Example 2-1 were intravenously administered to rats, wherein the vertical axis represents a concentration of the drug calculated as Dexamethasone (ng/ml) and the abscissa represents a time passage (hour) after administration: a curve connected with ● and a curve connected with ○ represent the test sample and the comparative sample, respectively.

Change in the total radioactivity in plasma when the test sample and the comparative sample were intravenously administered in the tail vein of SD strain male rats (weighing about 210 g) in a dose of 0.05 mg/kg calculated as Dexamethasone is shown in FIG. 2, when calculated as Dexamethasone. The comparative sample rapidly disappeared from plasma but disappearance of the test sample was gentle. Half life periods in the distribution phases were 10.5 minutes and 5.5 minutes, respectively.

Test Example 2-2

Delivery of the drug into an inflammatory region induced by carrageenin edema was compared between the test sample and the comparative sample, using the drug carrier of the present invention $^3$H-labeled Dexamethasone palmitate prepared in a manner similar to Example 4 as a test sample and the same comparative sample as used in Test Example 2-1.

TABLE 1

Delivery of Drug into Carrageenin Inflammatory Region:

|  |  | Test Sample | Comparative Sample |
|---|---|---|---|
| Paw with inflammation | (ng) | 475 ± 175 | 154 ± 17 |
|  | (ng/g) | 204 ± 53 | 64 ± 8 |
| Control paw | (ng) | 164 ± 19 | 89 ± 24 |
|  | (ng/g) | 94 ± 8 | 52 ± 14 |
| Edema region | (ng/g) | 538 ± 142 | 94 ± 42 |
| Plasma | (ng/g) | 448 ± 38 | 122 ± 12 |

Indication is (mean ± standard deviation)

Carrageenin edema was induced by subcutaneously administering 0.1 ml of 0.5% λ-carrageenin to SD strain male 20 rats (weighing about 195 g) at one paw heel. Two hours after the administration of carrageenin, the test sample and the comparative sample were intravenously administered in the tail vein in a dose of 0.5 mg/kg when calculated as Dexamethasone. Sixty minutes after the intravenous administration, blood was collected from the aorta in the abdomen to obtain plasma. At the same time, the paw with inflammation and the opposite paw (control paw) were cut off from the ankle joint. Radioactivity of each was measured after treating with a sample oxidizer.

In Table 1, with respect to the test sample, large amounts of the drug were transferred into the inflammatory region (edema region) and strong accumulation onto the inflammatory region was noted, as compared to the comparative sample. A drug concentration of 5.7 times that of the comparative sample was noted in the edema region induced by inflammation.

Test Example 2-3

Table 2 indicates the results of comparison in delivery of a drug into the hydrothorax and the major organs, in rats with pleurisy model, using the same test sample and comparative sample as used in Test Example 2-2 described above.

2% λ-Carrageenin, 0.1 ml, was administered to SD strain male rats (weighing about 300 g) at the thoracic cavity. Two and half hours after the administration of carrageenin, the test sample and the comparative sample were intravenously administered in the tail vein in a dose of 1.25 mg/kg when calculated as Dexamethasone. Thirty minutes after the intravenous administration, blood was collected from the aorta in the abdomen and fluid in the thoracic cavity was washed out with physiological saline to make 10 ml. Its radioactivity was determined. At the same time, the major organs were ectomized. Each radioactivity was measured after treating with a sample oxidizer.

TABLE 2

Transfer into Inflammatory Region and Major Tissues

|  |  | Test Sample | Comparative Sample |
|---|---|---|---|
| Fluid in the thoracic cavity | (μg) | 2.65 | 0.68 |
| Diaphragm | (μg/g) | 1.06 | 0.68 |
| Spleen | (μg/g) | 3.05 | 27.34 |
| Liver | (μg/g) | 7.71 | 17.84 |
| Heart | (μg/g) | 1.53 | 1.53 |
| Lung | (μg/g) | 2.36 | 1.93 |
| Kidney | (μg/g) | 2.66 | 1.37 |
| Plasma | (μg/ml) | 10.07 | 2.37 |

Indication is a mean value when converted into Dexamethasone.

In Table 2, with respect to the test sample, large amounts of the drug were delivered into the inflammatory region (hydrothoracic region) and strong accumulation onto the inflammatory region was noted, as compared to the comparative sample. A drug concentration of 3.9 times that of the comparative sample was noted in the fluid in the thoracic cavity. In distribution into the major organs, the test sample showed extremely low transfer in transfer into organs having developed reticuloendothelial system such as liver and spleen.

Test Example 2-4

The same test sample and comparative sample as used in Test Example 2-2 described above were intravenously administered to BALB/C male mice (weighing about 25 g). Thirty minutes after the administration, a concentration of the unchanged drug and a concentration of Dexamethasone as its metabolite were determined in plasma and liver. The dose was made 5 mg/kg when calculated as Dexamethasone.

Table 3 shows each concentration of the unchanged drug (Dexamethasone palmitate, its concentration was converted into Dexamethasone) and its metabolite (Dexamethasone) separately determined quantitatively.

In the case of the test sample, a concentration in plasma was high and distribution in the liver was low. Further the test sample was mostly present in plasma as the unchanged drug. In the case of using the drug carrier of the present invention, maintenance of blood concentration of the drug and a preventive effect in uptake into thereticuloendothelial system are clearly noted.

TABLE 3

|  | Test Sample (μg/ml, g) | Comparative Sample (μg/ml, g) |
|---|---|---|
| Unchanged drug in plasma | 36.3 ± 2.2 | 7.7 ± 1.6 |
| Dexamethasone in plasma | 4.6 ± 0.5 | 5.2 ± 0.9 |
| Unchanged drug in Liver | not detectable | not detectable |
| Dexamethasone in Liver | 24.0 ± 1.2 | 41.0 ± 1.3 |
| Liver/Plasma ratio in concentration (total amount) | 0.6 ± 0. | 3.0 ± 0.5 |

Indication is (mean ± standard deviation)

Test Example 5

With respect to the same test sample and comparative sample as used in Test Example 2-2 and a physiological saline solution of Dexamethasone phosphate, their pharmacological effects were examined using carrageenin edema inhibition as the index.

λ-Carrageenin (0.5%, 1 ml) was subcutaneously administered to SD strain male rats (weighing about 160 g) at one paw heel. Thirty minutes after, the test sample, the comparative sample and Dexamethasone phosphate were intravenously administered in the tail vein. For the control group, physiological saline was administered. A volume of the paw was measured prior to the administration of carrageenin and 5 hours after the administration in a conventional manner to determine an edema inhibition ratio.

Figure 3:
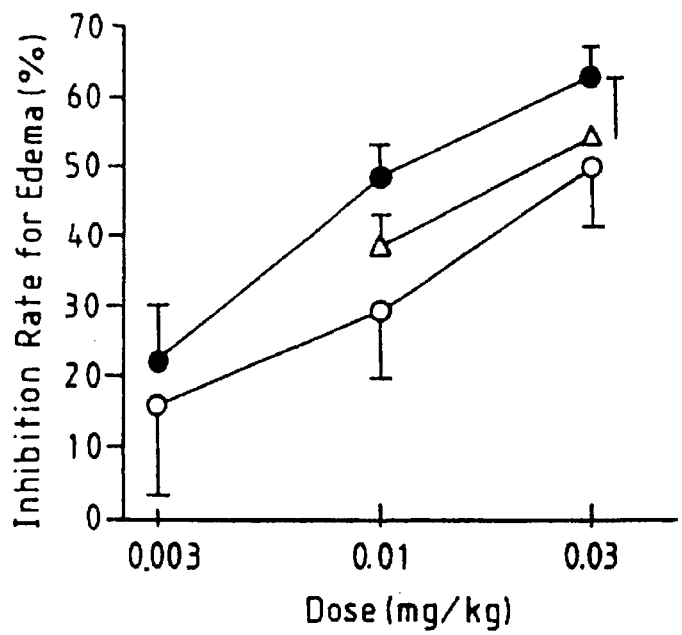
FIG. 3 is a dose-response curve of anti-inflammatory activity obtained using a carrageenin edema inhibition rate as the index, when the test sample and the comparative sample examined in Test Example 2-2 were intravenously administered to rats, wherein the vertical axis represents an inhibitory rate of carrageenin edema by % and the abscissa represents a dose of the drug calculated as Dexamethasone on a logarithmic scale: a curve connected with ●, a curve connected with ▲ and a curve connected with ○ represent the test sample, Dexamethasone phosphate and the comparative sample, respectively.

FIG. 3 shows its dose-response curve (indicated as Dexamethasone calculated). Table 4 shows a 50% edema inhibition dose ($ED_{50}$).

It is apparent that the test sample had an anti-inflammatory activity by about twice that of the other two samples, even in inflammation of this kind which was not improved with the comparative sample of the prior art. That is, the effect of the drug carrier of the present invention was confirmed as an effect of enhancing the drug effect. It is thus clear that this is because the drug is efficiently delivered to the focal lesion by using the drug carrier of the present invention.

TABLE 4

50% Edema Inhibition Dose

|  | $ED_{50}$ (ma/kg) |
|---|---|
| Test Sample | 0.012 |
| Comparative Sample | 0.031 |
| Dexamethasone phosphate | 0.023 |

(Indication is made by conversion into Dexamethasone)

Test Example 2-6

With respect to the same test sample and comparative sample as used in Test Example 2-2 and a physiological saline solution of Dexamethasone phosphate, their pharmacological effects were examined by the inhibition of carrageenin granuloma as the index. Further, weights of thymus and adrenals were examined.

λ-Carrageenin (2.0%, 4.0 ml) was subcutaneously administered to SD strain male rats (weighing about 160 g) at the back. From on Day 5, each sample was intravenously administered in the tail vein once daily for 3 days 3 times in total. A dose of the drug administered was made 0.05 mg/kg/once. For the control group, physiological saline was administered. Eight days after, granuloma, thymus and adrenal were ectomized and their weights were measured.

Figure 5:
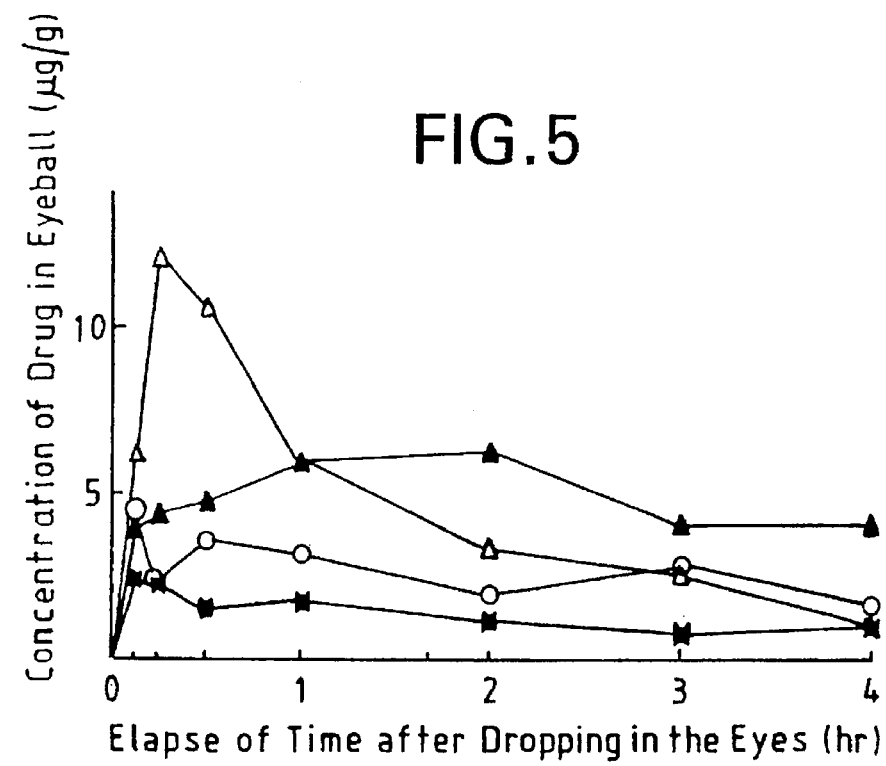
FIG. 5 represents amount of the drug delivered to the eyeball after applying the two test samples and the two comparative samples examined in Test Example 2-10, wherein the vertical axis represents a concentration (mg/ml, calculated as guaiazulene) of the drug in the eyeball and the abscissa represents passage of time (hour) after application to the eye: a curve connected with ▲, a curve connected with △, a curve connected with ■ and a curve connected with ⊙ represent Test Sample-(1), Test Sample-(2), Comparative Sample-(1) and Comparative Sample-(2), respectively.

It is noted from FIG. 5 that the test sample showed obviously strong granuloma formation inhibition activity as compared to the comparative sample and Dexamethasone phosphate and also showed less atrophy in the thymus and the adrenals. That is, it is shown that the test sample had a strong pharmacological effect but less side effects.

TABLE 5

Weights of granuloma, thymus and adrenal

|  | Granuloma | Thymus | Adrenal |
|---|---|---|---|
| Control | 20.5 ± 5.4 g | 416.0 ± 63.3 mg | 55.2 ± 9.6 mg |
| Test Sample | 10.9 ± 1.4 g | 205.0 ± 57.2 mg | 44.5 ± 7.2 mg |
| Comparative Sample | 15.5 ± 2.6 g | 149.8 ± 31.3 mg | 39.6 ± 2.7 mg |

Indication is (mean ± standard deviation)

Test Example 2-7

In order to confirm deliverability to the tumor region, a test was performed.

P388 leukemia cells, $10^6$ cells, were subcutaneously transplanted to CDF1 male mice (weighing about 25 g) at the right front limb. Six days after, the right front limb was cut out and provided for the experiment 5 days after. By this treatment, metastatic cancer model into the right upper arm and the right axilla lymph nodes was obtained. As the test sample, the drug carrier of the present invention prepared in Example 8 using $^3$H-labeled cholesteryl linoleate was used. As the comparative sample, a fat emulsion having a diameter of 0.2 µm, composed of refined soybean oil and yolk lecithin hitherto known in which $^3$H-labeled cholesteryl linoleate had been incorporated, was used. The test sample and the comparative sample were intravenously administered in the tail vein and 60 minutes after, the right upper arm and the right axilla lymph nodes in which tumor metastasis was noted were ectomized. Further as a non-metastatic lymph node, the left upper arm and the left axilla lymph nodes were simultaneously ectomized. Radioactivity of each was measured. As shown in Table 6, the drug carrier of the present invention was transferred to the tumor region in a concentration as high as twice or more. In the comparative sample, such a selective delivery in a high concentration was not noted.

TABLE 6

Delivery to Metastatic Lymph Node tumor

|  | Test Sample | Comparative Sample |
| --- | --- | --- |
| Metastatic lymph nodes | 2.60 ± 0.87 | 0.91 ± 0.27 |
| Non-metastatic lymph nodes | 1.04 ± 0.27 | 0.86 ± 0.39 |

Indication is (% of dose/g, mean ± standard deviation)

Test Example 2-7a

A test confirming a transfer to tumor region was conducted.

S-180 tumor cells (1×10$^6$) were inoculated subcutaneously to the abdominal skin of ddY strain mice (body weight: ca. 25 g) After 6 days, diameter of the tumor became about 1 cm and it was subjected to a test.

As to sample, the pharmaceutical carrier of the present invention in Example 8 prepared from $^3$H-labelled cholesteryl linoleate was used. As a control, $^3$H-labelled cholesteryl linoleate was made incorporated into fat emulsion comprising yolk lecithin and soybean oil of 0.2 micron diameter and the product was used.

Both sample and control were administered in the tail vein, then tumor was taken out after 15 minutes, 1 hour and 24 hours, and the radioactivity was determined.

As shown in Table 6a, the carrier of the present invention was transferred, in each time tested, to the tumor region at the concentration of about three times as much as compared with the control.

TABLE 6a

|  | Transfer to Solid Tumor | |
| --- | --- | --- |
| Time | Tested Sample | Control |
| 0.25 hr | 1.37 ± 0.34 | 0.35 ± 0.14 |
| 1 | 1.64 ± 0.21 | 0.54 ± 0.13 |
| 24 | 6.59 ± 0.38 | 2.96 ± 1.22 |

The figures are in % of dose/g; average ± standard deviation.

Test Example 2-8

For purposes of confirming stability of the drug carrier of the present invention in the body in which cholesteryl linoleate was the core, the drug carrier of the present invention obtained in Example 5 was used as a test sample and as a comparative sample, the drug carrier of the present invention obtained in Example 4 was used. These samples were intravenously administered to rats, respectively. Change in blood concentration was determined. Samples prepared using $^3$H-labeled Dexamethasone palmitate as the respective samples.

Figure 4:
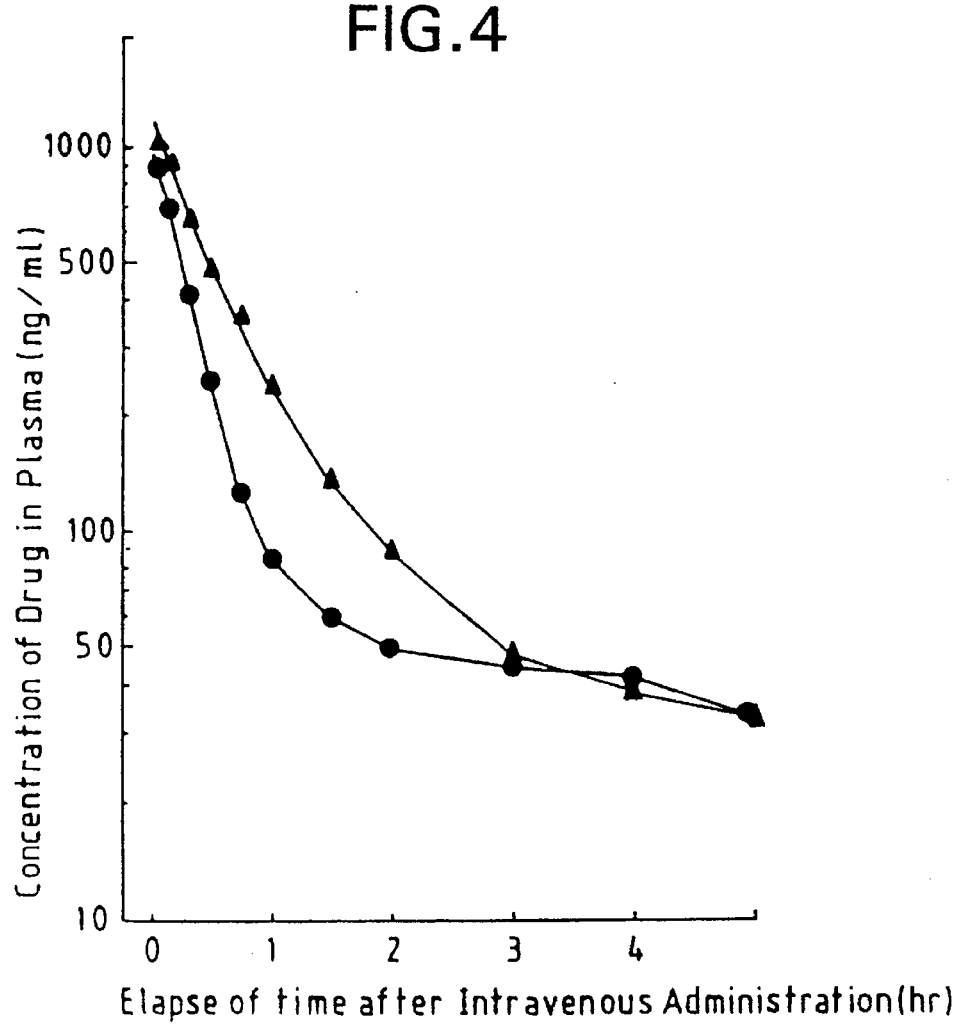
FIG. 4 represents change of the total radioactivity in plasma when the test sample and the comparative sample examined in Test Example 2-8 were intravenously administered to rats, wherein the vertical axis represents a concentration (mg/ml) of Dexamethasone calculated from the radioactivity and the abscissa represents passage of time (hour) after administration: a curve connected with ▲ and a curve connected with ● represent the test sample and the comparative sample, respectively.

Change in total radioactivity in plasma when the test sample and the comparative sample were intravenously administered to SD male rats (weighing about 250 g) in the tail vein in a dose of 0.05 mg/kg when calculated as Dexamethasone is shown in FIG. 4, when calculated as Dexamethasone. The test sample disappeared from plasma more gently than the comparative sample. Half lives for the disappearance in the distribution phase were 21.6 minutes and 11.5 minutes, respectively.

Test Example 2-9

The test samples obtained in Examples 3, 4 and 5 and the comparative sample used in Test Example 2-1 were mixed with rat plasma, respectively, to examine the stability. The concentration of the sample in plasma was 23 µg/ml when calculated as Dexamethasone. As shown in Table 7, the amount of the unchanged drug (Dexamethasone palmitate) remained after incubation at 37° C. for 90 minutes, namely, stability in plasma, was obviously superior in the drug carrier of the present invention to the comparative sample.

In addition, it was also confirmed that using cholesteryl linoleate as the core of the drug carrier of the present invention increased the stability depending upon its content.

TABLE 7

Stability in Plasma

|  | Remaining Amount of Unchanged Drug |
| --- | --- |
| Test Sample obtained in Example 3 | 39.8% |
| Test Sample obtained in Example 4 | 47.5% |
| Test Sample obtained in Example 5 | 68.1% |
| Comparative Sample of Test Example 2-1 | 20.1% |

Test Example 2-10

After applying an eye drop of test preparation to the eye of ddY mice (weighing about 30 g) under anesthesia with pentobarbital, a drug concentration in the eyeball was measured and deliverability of the drug into the eyeball was examined.

Test preparations are below:

| Test sample - (1) | drug carrier of the present invention containing anti-inflammatory guaiazulene obtained in Example 1 |
| --- | --- |
| Test sample - (2) | drug carrier of the present invention containing anti-inflammatory guaiazulene obtained in Example 2 |
| Comparative sample - (1) | fat emulsion having a diameter of 0.2 µm composed of soybean oil and yolk lecithin according to the prior art in which guaiazulene had been incorporated |
| Comparative sample - (2) | fat emulsion having a diameter of 0.2 µm composed of soybean oil and yolk lecithin according to the prior art in which sodium guaiazulene-3-sulfonate as a water soluble derivative of guaiazulene had been mixed and dissolved. |

A dose was made 5 µg/eye when calculated as guaiazulene. After applying to the eye, the eyeball was ectomized in a definite time. After immediately washing with physiological saline, the eyeball was homogenized and the drug was determined by high performance liquid chromatography.

Change in the drug concentration in the eyeball is shown in FIG. 5. The test samples all showed better deliverability to the eyeball than the comparative samples. It is evident that delivery of the drug into the eyeball was improved in the case of using the drug carriers of the present invention.

Test Example 2-11

Using the drug carrier containing guaiazulene obtained in Example 1 as a test sample and a water soluble derivative of guaiazulene, sodium guaiazulene-3-sulfonate, as a comparative sample, these samples were applied to the eye of Japanese white rabbits (weighing about 3 kg) to examine delivery of the drug to the aqueous humor. Thirty minutes after the eyedropping, the aqueous humor was collected and the drug concentration was measured. The results are shown in Table 8. Only in the case of using the drug carrier of the present invention, delivery of the drug to the aqueous humor was noted.

TABLE 8

Delivery of Drug to Aqueous Humor after Application to the Eye

| Test Sample | 3.47 ± 3.31 |
|---|---|

Comparative Sample not detectable
Indication is (mean ± standard deviation)

Test Example 2-12

Using the drug carrier of the present invention containing antihistaminic Diphenhydramine obtained in Example 6 as a test sample and a Diphenhydramine hydrochloride solution in physiological saline as a comparative sample, a preventive action against accentuation of vasopermeability induced by intracutaneous administration of histamine was examined.

The test sample or the comparative sample were intravenously administered to SD strain male rats (weighing about 300 g). After a definite time period, 10 mg of Evans Blue was intravenously administered and at the same time, histamine hydrochloride (1 µg/50 µl) was intracutaneously injected to the abdominal skin. Further 30 minutes after, the skin was peeled apart to quantitatively determine Evans Blue exudate into the skin. After the skin was solubilized with 3 ml of conc. hydrochloric acid, 3 ml of 10% benzalconium chloride was added to the solution, Evans Blue was extracted with 5 ml of chloroform. An amount of Evans Blue exudate into the skin was determined by absorbance at 620 nm in the chloroform layer.

Figure 6:
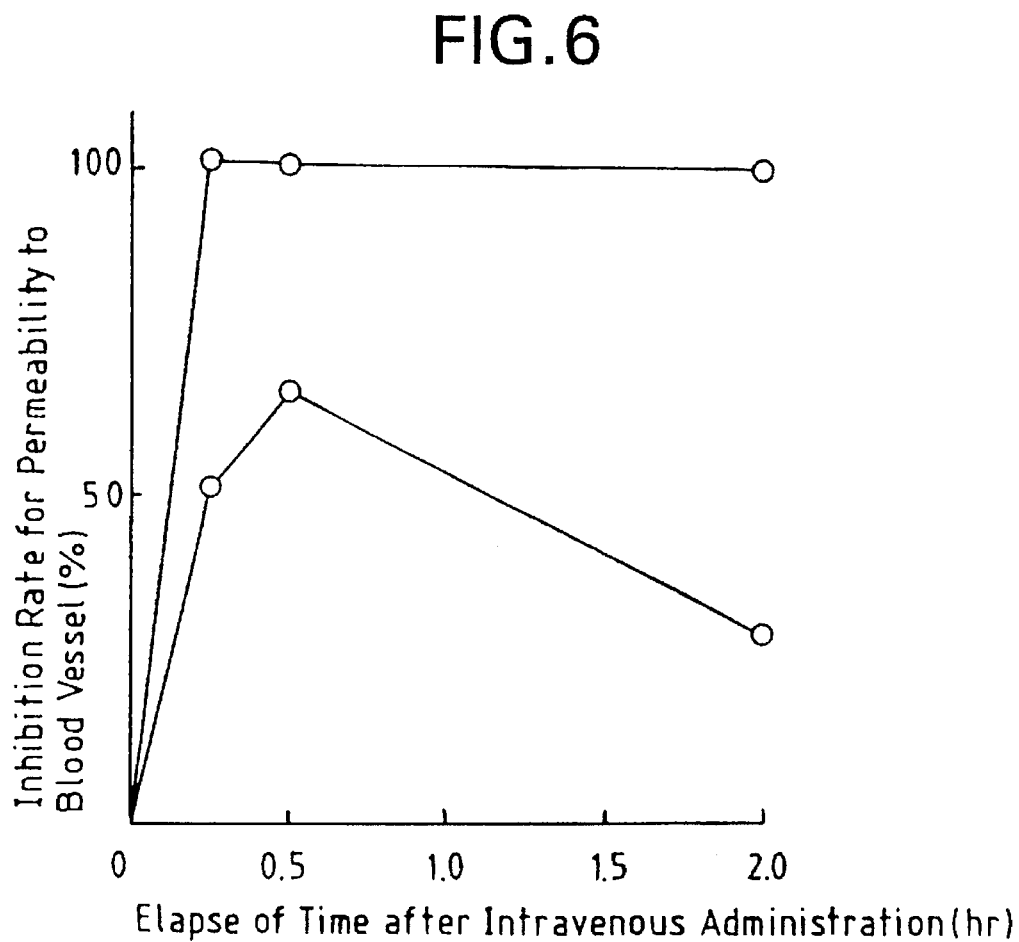
FIG. 6 represents the time courses of the inhibition of the vasopermeability when test sample and the comparative sample examined in the Test Example 2-12 were intravenously administered to rats, wherein the vertical axis represents the inhibition of the vasopermeability in percent and the abscissa represents passage of time (hour) after administration of the sample.

FIG. 6 shows time-dependent change of the inhibition of the vasopermeability induced by intracutaneously injecting histamine 15, 30 and 120 minutes after administration of both samples, doses of which were made 2 mg/kg when calculated as Diphenhydramine. The test sample showed the maximum effect already 15 minutes after the administration. The effect was continued up to 2 hours. On the other hand, in the comparative sample, its inhibition rate was lower than the test sample. The comparative sample showed the maximum effect 30 minutes after the administration and the effect was then decreased. The test sample showed the inhibition of the vasopermeability by 3 times or more than the comparative sample 2 hours after the administration. By the results, it is shown that the test sample not only enhances the drug effects but also has an effect of duration in the drug action.

FIG. 7 shows a dose-response curve showing the inhibition of vasopermeability obtained 30 minutes after administration of the samples. It is evident that the test samples are excellent in the inhibition of the vasopermeability as compared to the comparative sample.

The present invention has particular utility in the administration of polyene antifungal antibiotics.

Polyene antifungal antibiotics, represented by amphotericin B and the advent of which dates back about 30 years ago, are still of great use as antifungal agents for systemic administration with good assurance of effect.

However, these agents have the drawback that their serious side effects, such as hemolytic toxicity and nephrotoxicity, detract seriously from their therapeutic utility and prevent institution of adequate therapy.

Furthermore, for the preparation of injections, these agents require sodium deoxycholate, which is a surfactant having irritating and hemolytic potentials, and in this respect there has been a standing demand for improvements in dosage forms and formulations.

Recently, for the purpose of reducing the risks of polyene antifungal antibiotics for side effects, it has been proposed and practiced to administer them in the form of a phospholipid-based liposome preparation or a fat emulsion based on soybean oil emulsifed with a small amount of phospholipid. (Szoka, F. C. Jr., et al., Antimicrobial Agents and Chemotherapy, 31, 421–429, 1987 [hereinafter referred to as literature 1-1], Kirsh, R. et al., Journal of Infectious Diseases, 158, 1065–1070, 1988 [hereinafter referred to as literature 1-2], Japanese Patent Application Kokai No. 63-66123 [hereinafter referred to as literature 1-3], etc.)

However, while these liposome preparations and fat emulsions have successfully reduced the risks of polyene antifungal antibiotics for hemolytic toxicity and acute toxicity, these preparations still have a serious drawback in that they have little effect in reducing the nephrotoxic potential of the antibiotics which is the most important factor in clinical medicine.

In addition, while these liposome preparations and fat emulsions are characterized in that they are phagocytized by the macrophages etc. concentrated at the focus of infection, they have the disadvantage that when viewed at the systemic level, more than a half of the drug administered is phagocytized, in the course of translocation, by the cells of the reticuloendothelial systems represented by the liver and spleen so that the intrinsic transfer of the drug to the infection site is not necessarily high.

On the other hand, from the standpoints of the art of pharmaceutical manufacture and the stability of preparations, liposomes do not lend themselves to commercial high-production processes and are also seriously lacking in shelf-life in terms of increases in the size of vescicles due to flocculation.

Furthermore, the various fat emulsions heretofore used clinically as hyperalimentation fluids have been applied as injection dosage forms for various drugs and their utility is well known, but the application thereof to any polyene antifungal antibiotic presents many production and stability problems because, for example, drugs in this class are amphiphilic and only sparingly soluble in soybean oil.

In view of the circumstances, the inventors of the present invention searched for a dosage form which would not affect the basic mechanism of pharmacologic action (antifungal action) of polyene antifungal antibiotics at the molecular level, yet still reduce their hemolytic toxicity and nephrotoxicity and, furthermore, be improved in the transfer of the active drug to the infection site. The present invention has been conceived and developed on the basis of the above research.

It is an object of the present invention to provide a pharmaceutical preparation by which therapeutically effective amount of a polyene antifungal antibiotic can be delivered to the target site without fear of induction of serious renal disorder by reducing the nephrotoxicity of the antibiotic which is the most onerous and intrinsic problem in clinical practice.

The average particle diameter of the fat emulsion according to the invention is not less than 10 nm and not more than 100 nm. Thus, at the site of increased vascular permeability associated with an inflammatory reaction due to fungal infection, the emulsion particles are ready to migrate from within the blood vessel into the lesioned tissue.

In other words, at the infection site, a large number of emulsion particles of the invention selectively find their way from the blood vessel to the affected tissue. At the same time, the drug as entrapped in the emulsion particles is readily and selectively transported to the focus of infection. Since the drug is thus easily and selectively delivered to the lesion, the local drug concentration at the site is increased and, hence, an enhanced response to the drug can be assured.

The average particle size of the fatty emulsion according to the invention is desirably less than 100 nm, preferably not less than 5 and particularly 10 to 70 nm, especially 15 to 50 nm. As shown in the examples, means particle diameters in the range of from about 16 nm to about 48 nm are especially useful. The emulsion particles in these size ranges are superior in evading uptake by the reticuloendothelial system.

In addition, with the fatty emulsion of the invention, the untoward effect of the polyene antifungal antibiotic on renal function is not found at all. This can be interpreted to mean that with the fat emulsion of the invention, the amount of transport of the polyene antifungal antibiotic to the kidney can be minimized so that diminution of the damage to the kidney is accomplished.

Another feature of the present invention resides in the use of finely-divided stable emulsion particles for the delivery of polyene antifungal antibiotics.

This reduction of emulsion particle size not only assures the aforesaid effects but also inhibits the nonspecific uptake of drugs into the reticuloendothelial tissues to thereby assure sustained blood concentrations.

Polyene antifungal antibiotics are comparatively labile drugs and known to decompose by degrees in aqueous solution. In the present invention, however, the polyene antifungal antibiotic exists as secluded from the surrounding environment because it has been entrapped in lipid droplets, with the result that it is protected against enzymatic and non-enzymatic degradation, thus contributing to an improved stability of the drug.

The fatty emulsion of the invention is generally administered into the vein of animals including humans for the treatment and prevention of fungal injections, viral infections and so on.

While the dosage of the fatty emulsion of the invention varies with different routes of administration, clinical conditions or symptoms, purposes of administration, etc., it is generally sufficient to use 1 to 1000 ml, as emulsion, per dose. The dosage of the polyene antifungal antibiotic is generally 1 to 200 mg/dose per adult human.

As examples of the polyene antifungal antibiotic which can be used in accordance with the invention, there may be mentioned not only amphotericin B but also amphotericin B methyl ester, nystatin, trichomycin, pimaricin and so on.

In accordance with the present invention, the clinical usefulness of polyene antifungal antibiotics can be remarkably enhanced. Among the effects of the invention which have been realized by overcoming the drawbacks of the prior art are (1) marked alleviation of the hemolytic toxicity of polyene antifungal antibiotics and of the nephrotoxicity thereof which is the truly important problem to be solved, (2) improvement of the transfer kinetics of the drug to lesions, (3) suppression of uptake of the drug in the reticuloendothelial system, (4) realization of sustained blood concentration of the active drug, (5) improvement of storage stability, and (6) reduction of manufacturing cost. These effects have been brought into being only by the present invention.

EXAMPLES

The following examples, each pertaining to the manufacture of the fatty emulsion of the invention, are intended to illustrate the invention in further detail and should by no means be construed as defining the metes and bounds of the invention.

Production Example 3-1

In 100 ml of chloroform-methanol (1:1, v/v) are dissolved 3 mg of amphotericin B, 0.5 g of purified soybean oil and 0.5 g of purified egg yolk lecithin and using a rotary evaporator, the solvent is thoroughly evaporated under reduced pressure.

The residue is then diluted with 8 ml of isotonized phosphate buffer and stirred using a homogenizer to give a crude emulsion. This emulsion is made up to 10 ml with isotonic phosphate buffer and further emulsified in an ultrasonic homogenizer (Branson Model 185) under ice-cooling for 60 minutes to give an ultrafine fatty emulsion containing amphotericin B.

Production Example 3-2

At a temperature of about 60° C., 3 g of amphotericin B, 50 g of purified soybean oil and 15 g of purified egg yolk lecithin are mixed well, followed by addition of 500 ml of isotonic phosphate buffer, and the mixture is stirred in a homo-mixer to give a crude emulsion. This crude emulsion is further emulsified at a high pressure using a Manton Gaulin type homogenizer to give an ultrafine fatty emulsion containing amphotericin B.

Production Example 3-3

In 100 ml of chloroform-methanol (1:1, v/v) are dissolved 30 mg of amphotericin B, 0.6 g of purified soybean oil and 0.5 g of egg yolk lecithin and using a rotary evaporator, the solvent is thoroughly removed under reduced pressure. The residue is diluted with 8 ml of a 0.24M aqueous solution of glycerol and stirred in a homogenizer to give a crude emulsion. This crude emulsion is made up to 10 ml with a 0.24M aqueous solution of glycerol and further homogenized in an ultrasonic homogenizer (Branson Model 185) under ice-cooling for 60 minutes to give an ultrafine fatty emulsion containing amphotericin B.

Production Example 3-4

At a temperature of about 60° C., 2 g of amphotericin B, 20 g of purified soybean oil and 30 g of purified egg yolk lecithin are mixed well, followed by addition of 100 ml of a 0.24M aqueous solution of glycerol. The mixture is then stirred in a homo-mixer to give a crude emulsion. This crude emulsion is further emulsified at a high pressure in a microfluidizer to give an utltrafine fatty emulsion containing amphotericin B.

Production Example 3-5

In 100 ml of chloroform-methanol (1:1, v/v) are dissolved 1 mg of amphotericin B, 0.5 g of cholesteryl oleate and 0.5 g of purified egg yolk lecithin and using a rotary evaporator, the solvent is thoroughly removed under reduced pressure. The residue is then diluted with 8 ml of a 0.24M aqueous solution of glycerol and stirred in a homogenizer to give a crude emulsion. This crude emulsion is made up to 10 ml with a 0.24M aqueous solution of glycerol and, then, further emulsified in a homogenizer (Branson Model 185) for 60 minutes to give an ultrafine fatty emulsion containing amphotericin B.

Production Example 3-6

In 100 ml of chloroform-methanol (1:1, v/v) are dissolved 3 mg of amphotericin B, 0.5 g of purified soybean oil, 0.4 g of purified egg yolk lecithin and 0.1 g of dimyristoylphosphatidylglycerol, and using a rotary evaporator, the solvent is thoroughly removed under reduced pressure. The residue is then diluted with 8 ml of a 9% aqueous solution of lactose and stirred in a homogenizer to give a crude emulsion. This crude emulsion is made up to 10 ml with a 9% aqueous solution of lactose and further emulsified in an ultrasonic homogenizer (Branson Model 185) for 60 minutes to give an ultrafine fatty emulsion containing amphotericin B.

Production Example 3-7

In 100 ml of chloroform-methanol (1:1, v/v) are dissolved 3 mg of amphotericin B, 0.5 g of purified soybean oil, 0.4 g of hydrogenated egg yolk lecithin and 0.1 g of cholesterol and using a rotary evaporator, the solvent is thoroughly removed under reduced pressure. The residue is then diluted with 8 ml of a 9% aqueous solution of lactose and stirred in a homogenizer to give a crude emulsion. This crude emulsion is made up to 10 ml with a 9% aqueous solution of lactose and further emulsified in an ultrasonic homogenizer (Branson Model 185) for 60 minutes to give an ultrafine fatty emulsion containing amphotericin B.

Production Example 3-8

To each of the amphotericin B-containing compositions prepared in Production Examples 3-1, 3-5 and 3-6 is added 0.5 g of albumin and the mixture is lyophilized to give a freeze-dried preparation.

The results of the various tests performed for evaluating the characteristics of the amphotericin B-containing pharmaceutical compositions of the invention are set forth hereunder. In each test, a commercial amphotericin B preparation, several prior art amphotericin B liposome preparations and a prior art fatty emulsion were used as controls. The details of the respective samples are given below.

Test sample 4-1:

The amphotericin B preparation according to Production Example 3-1.

Test sample 4-2:

The amphotericin B preparation according to Production Example 3-3.

Control sample 5-1:

A commercial amphotericin B preparation for injection [trade name: Fungizone (registered trademark), Japan Squibb)

Control sample 5-2:

An amphotericin B-containing liposome preparation according to Literature 1-1, which is a multilamellar liposome preparation (dimyristoylphosphatidylcholine:dimyristoylphosphatidylglycerol=7:3, mole ratio).

Control sample 5-3:

An amphotericin B-containing liposome preparation according to Literature 1-1, which is a small-unilamellar liposome preparation subjected to ultrasonic treatment (dimyristoylphosphatidylcholine:dimyristoylphosphatidylglycerol=7:3)

Control sample 5-4:

An amphotericin B-containing liposome preparation according to Literature 1-1, which is a small-unilamellar liposome preparation based on purified egg yolk lecithin and subjected to ultrasonication.

Control sample 5-5:

An amphotericin B-containing fat emulsion according to Literature 1-2, which is based on purified soybean oil and purified egg yolk lecithin.

Test Example 6-1:

Hemolysis test

FIG. 8 shows the results of an in vitro hemolysis test using purified rat erythrocytes on Test Sample 4-1 and Control Sample 5-1. Whereas Control Sample 5-1 produced a marked hemolytic effect at very low amphotericin B concentrations, Test Sample 4-1 showed almost no hemolytic effect even at no less than 200-fold higher concentration. It is, thus, apparent that like the hithertoknown liposome preparation and fatty emulsion, the fatty emulsion of the invention markedly reduces the hemolytic toxicity of amphotericin B.

Test Example 6-2:

In vivo acute toxicity study

Using male ddY mice (body weights: ca. 20 g) as test animals, each of the test and control samples was administered into the caudal vein to evaluate its acute toxicity. FIGS. 9 and 10 show the survival rates of mice at 1 hour and 72 hours, respectively, after single administration of the respective samples.

The survival rates at 1 hour after administration, which are shown in FIG. 9, represent the toxicity attributable, for the most part, to the hemolytic activity of amphotericin B. Both test samples were very low in toxicity. Among the control samples, Samples 5-2 and 5-3 showed reductions in hemolytic toxicity. However, Control Samples 5-1, 5-4 and 5-5 failed to show any reduction in acute toxicity. The survival rates at 72 hours after administration, which are shown in FIG. 10, represent the toxicity attributable, for the most part, to the nephrotoxicity of amphotericin B. Both test samples were very low in toxicity. In contrast, all the control samples showed toxicity, indicating that they are more injurious to the kidney than the test samples.

It is, thus, clear that compared with the conventional liposome preparation and fatty emulsions, the fatty emulsions of the presently invention are markedly alleviated in toxicity, not only in the aspect of hemolytic toxicity which can be assessed immediately after administration but also in the aspect of nephrotoxicity which is more reasonably evaluated at 72 hours after administration.

Test Example 6-3:

The concentration of the drug in the kidney (Transfer to the kidney)

Using male SD rats (body weights: ca. 250 g) as test animals, the test and control samples were respectively administered into the caudal vein of rats. The dosage was 1 mg (as amphotericin)/kg. The kidney was excised 18 hours after administration and homogenized, and the concentration of amphotericin B in the homogenate was determined by high performance liquid choromatography. The results are set forth in Table 1-1.

Whereas the concentrations of amphotericin B in the kidneys after administration of the test samples were invariably less than the detection limit, high levels of amphotericin B were found after administration of the control samples.

It is, thus, apparent that compared with the conventional liposome preparation and fatty emulsions, the fatty emulsions of the present invention have been improved in the translocation of the drug to the kidney (decreased transfer to the kidney).

TABLE 1-1

Transfer of amphotericin B to the kidney
Concentration in the kidney (μg/g)

| Test sample 4-1 | Less than detection limit (0.1) |
| Test sample 4-2 | Less than detection limit (0.1) |
| Control sample 5-1 | 1.4 ± 0.1 |
| Control sample 5-2 | 1.3 ± 0.3 |
| Control sample 5-5 | 1.5 ± 0.4 |

(Mean ± S.D., n = 3)

Test Example 6-4:
Renal function assay

Using male SD rats (body weights: ca. 250 g) as test animals, the test and control samples were respectively administered into the caudal vein. The dosage was 1 mg (as amphotericin)/kg and the intravenous administration was carried out for a total of 3 times. Twenty-four hours after the last administration, the blood was drawn from the jugular vein and the serum was separated. The serum urea nitrogen (BUN) as an indicator of renal function was then determined with a commercial assay kit. The results are set forth in Table 1-2. As a negative control, physiological saline was similarly administered and the serum was separated and assayed in the same manner.

TABLE 1-2

Renal function assay (serum biochemistry test)

| | BUN (mg/d) |
| --- | --- |
| Control | 14.7 ± 1.7 |
| Test sample 4-1 | 14.7 ± 1.2 |
| Test sample 4-2 | 16.5 ± 1.5 |
| Control sample 5-1 | 29.2 ± 2.6 |
| Control sample 5-2 | 29.9 ± 2.1 |
| Control sample 5-5 | 37.8 ± 5.4 |

(Mean ± S.D., n = 3)

The levels of BUN after administration of the test samples were not different from the negative control value, indicating that these preparations had no deleterious effect on renal function. In contrast, the administration of the control samples invariably caused marked elevations of BUN, indicating their adverse effect on renal function. It is, therefore, apparent that compared with the conventional liposome preparation and fatty emulsions, the fatty emulsions of the present invention have been considerably improved in decreasing the injurious effect on renal function.

Test Example 6-5
Time course of blood concentration

Using male SD rats (body weights: ca. 250 g) as test animals, the test and control samples were respectively administered into the caudal vein. The dosage was 1 mg (as amphotericin B)/kg. At predetermined intervals after administration, a small amount of blood was drawn from the jugular vein and the plasma was separated. The concentrations of amphotericin B in the plasma samples were determined by high performance liquid chromatography. The time-course data are presented in FIG. 11.

The plasma concentrations of amphotericin B after administration of the test samples were invariably higher than the corresponding concentrations for the control samples at any time point after administration. On the other hand, the plasma concentrations after administration of the control samples declined rapidly. It is, thus, clear that compared with the conventional liposome preparation and fatty emulsion, the fatty emulsion of the invention is conducive to a by far more sustained blood concentration of amphotericin B.

Test Example 6-6:
Transfer of the drug to the inflammation site

It is known that the site of fungal infection develops an inflammatory reaction. Therefore, using such an inflammation model in animals, the transferability of the drug to the inflammation site was investigated.

Thus, using male SD rats (body weights: ca. 250 g) as test animals, a pleurisy model was constructed by infusing 0.1 ml of 2% λ-Acarrageenin into the thoracic cavity of each animal. After an interval of 2.5 hours, the test and control samples were respectively administered into the caudal vein. The dosage was 1 mg (as amphotericin B)/kg. At predetermined intervals after administration, the animals were serially sacrificed by exsanguination from the abdominal aorta and the exudate was collected from the thoracic cavity. The concentration of amphotericin B in the exudate was determined by high performance liquid chromatography. The data are presented in FIG. 12. It was found that the concentrations of amphotericin B in the pleural exudates after administration of the test samples were invariably higher than those for any of the control samples at any time point after administration. It is, therefore, clear that compared with the conventional liposome preparation and fatty emulsions, the fatty emulsions of the invention are superior in the degree of focusing on the inflammation site (site of infection) and assures a more effective and safe therapeutic modality.

Test Example 6-7:
Determination of particle size

Using a particle size analyzer of laser dynamic light scattering type, the emulsion particle diameter of Test sample 4-1 was determined and evaluated. Test sample 4-1 had a particle size distribution in the range of about 20 to 80 nm and was free from particles over 1μ.

It is, thus, apparent that the fatty emulsions of the present invention are made up of extremely fine and uniform emulsion particles. Furthermore, since these fatty emulsions do not contain particles over 1μ which are toxicologically objectionable, they are conducive to an effective and safe drug therapy.

Test Example 6-8:
In vitro antifungal activity assay

Candida albicans was grown on Sabouraud's media, and by adding the test and control samples to the media, the minimal concentration of amphotericin B required to inhibit growth of the organism was determined. Based on the data, the antifungal activity of each sample was evaluated. As shown in Table 1-3, all the samples inhibited growth of the candial organism at very low levels of amphotericin B.

The fatty emulsions of the present invention had no adverse effect on the inherent antifungal activity of amphotericin B, suggesting that they assure an effective and safe therapeutic modality.

TABLE 1-3

Antifungal activity (In vitro)

| | Minimum effective concentration (μg/ml) |
| --- | --- |
| Test sample 4-1 | Not more than 0.03 |
| Test sample 4-2 | Not more than 0.16 |
| Control sample 5-1 | Not more than 0.20 |
| Control sample 5-3 | Not more than 0.14 |

The present invention also has particular utility in the administration of imidazole fungicides.

A variety of imidazole fungicides have excellent fungicidal activity and have already been used for treating various infectious diseases in the clinical field.

For example, Miconazole, which is representative of imidazole fungicides, is an important fungicide which can be generally administered and is expectable to be effective with certainty.

However, to make its injection preparations, it was necessary to solubilize Miconazole using a surface active agent such as polyoxyethylene-hardened castor oil (HCO-60), etc. because the fungicide is sparingly soluble in water.

It was recently found that this surface active agent HCO-60 caused anaphylaxic shock and was questionable as an additive to drugs. Therefore, its preparations involve problems in that the clinical use is strictly restricted and hence, medical treatment cannot be sufficient. Thus, an improvement has been desired.

The present inventors have made continuous investigations with attempts to prepare medical preparations containing sparingly water-soluble imidazole fungicides without containing any harmful surface active agent such as polyoxyethylene-hardened castor oil (HCO-60), etc. and further to provide preparation forms having excellent transfer of drugs into the infected lesion without affecting molecular level pharmacological mechanism (fungicidal activity) possessed by imidazole fungicides. As a result, they have finally succeeded in accomplishing the present invention.

The preparation comprising the fatty emulsions of the present invention are generally administered intravenously to human or various animals, for purposes of treating or preventing fungal infections or viral infections.

A dose of the preparation comprising the fatty emulsions of the present invention may vary depending upon route for administration, preparation form, condition and purpose but is generally preferably 1 to 1000 ml/time as the emulsion. A dose administered as the imidazole fungicide is generally 5 to 500 mg/time to adult.

As the imidazole fungicide which can be used in the present invention, compounds that are sparingly soluble in water are desired and Miconazole is most preferred.

According to the present invention, clinical value of the imidazole fungicide can be markedly enhanced. The effects of the present invention can be summarized in overcoming the prior art problems and providing novel, safe and more effective preparations of the imidazole fungicide that (1) pharmacological activity per se of the drug is not affected, (2) the drug is selectively transferred efficiently into lesional tissue, (3) blood concentration of the drug can be maintained over long periods of time, (4) a necessary dose of the drug can be reduced, and (5) no harmful additive is used and as a result, they have finally succeeded in accomplishing the present invention. These effects have been achieved by the present invention for the first time.

The constituent components of the fatty emulsions of the present invention are mainly composed of medically acceptable lipids which have been heretofore used as medicines in the clinical field and therefore, can be extremely safe when used. This is also one of the important effects of the present invention.

EXAMPLES

Hereafter the present invention is explained in more detail by referring to examples relating to the preparation of the fat emulsion of the present invention, but the present invention is not deemed to be limited thereto.

Preparation Example 7-1

After 3 mg of Miconazole, 0.5 g of purified soybean oil and 0.5 g of purified yolk lecithin were mixed with and dissolved in 100 ml of a mixture of chloroform/methanol (1/1, v/v), the solvent was completely removed under reduced pressure using a rotary evaporator. To the residue was added 8 ml of 0.24M glycerine aqueous solution. The mixture was stirred with a homogenizer to form a crude emulsion. By adding 0.24M glycerine aqueous solution to make the volume 10 ml, the mixture was emulsified for 60 minutes under ice-cooling using an ultrasonic homogenizer (Branson Model 185) to give an ultrafine fatty emulsion containing Miconazole.

Preparation Example 7-2

After 29 mg of Miconazole, 0.25 g of purified soybean oil and 0.25 g of purified yolk lecithin were mixed with and dissolved in 100 ml of a mixture of chloroform/methanol (1/1, v/v), the solvent was completely removed under reduced pressure using a rotary evaporator. To the residue was added 8 ml of isotonic phosphate buffer solution. The mixture was stirred with a homogenizer to form a crude emulsion. By adding isotonic phosphate buffer solution to make the volume 10 ml, the mixture was emlusified for 60 minutes under ice-cooling using an ultrasonic homogenizer (Branson Model 185) to give an ultrafine fatty emulsion containing Miconazole.

Preparation Example 7-3

After 2 g of Miconazole, 20 g of purified soybean oil and 30 g of purified yolk lecithin were heated to about 60° C. to mix them with each other, 500 ml of 0.24M glycerine aqueous solution was added to the mixture. The mixture was stirred with a homomixer to form a crude emulsion. The crude emulsion was emulsified under high pressre using a microfluidizer to give an ultrafine fatty emulsion containing Miconazole.

Preparation Example 7-4

After 1 mg of Miconazole, 0.5 g of cholesteryl oleate and 0.5 g of purified yolk lecithin were mixed with and dissolved in 100 ml of a mixture of chloroform/methanol (1/1, v/v), the solvent was completely removed under reduced pressure using a rotary evaporator. To the residue was added 8 ml of 0.24M glycerine aqueous solution. The mixture was stirred with a homogenizer to form a crude emulsion. By adding 0.24M glycerine aqueous solution to make the volume 10 ml, the mixture was emulsified for 60 minutes using an ultrasonic homogenizer (Branson Model 185) to give an ultrafine fatty emulsion containing Miconazole.

Preparation Example 7-5

After 3 mg of Miconazole, 0.5 g of purified soybean oil, 0.4 g of purified yolk lecithin and 0.1 g of dimyristoylphosphatidylglycerol were mixed with and dissolved in 100 ml of a mixture of chloroform/methanol (1/1, v/v), the solvent was completely removed under reduced pressure using a rotary evaporator. To the residue was added 8 ml of 9% lactose aqueous solution. The mixture was stirred with a homogenizer to form a crude emulsion. By adding 9% lactose aqueous solution to make the volume 10 ml, the mixture was emulsified for 60 minutes using an ultrasonic homogenizer (Branson Model 185) to give an ultrafine fatty emulsion containing Miconazole.

Preparation Example 7-6

After 5 mg of Miconazole, 0.5 g of purified soybean oil, 0.4 g of hydrogenated yolk lecithin and 0.1 g of cholesterol were mixed with and dissolved in 100 ml of a mixture of chloroform/methanol (1/1, v/v), the solvent was completely removed under reduced pressure using a rotary evaporator. To the residue was added 8 ml of 9% lactose aqueous solution. The mixture was stirred with a homogenizer to form a crude emulsion. By adding 9% lactose aqueous solution to make the volume 10 ml, the mixture was emulsified for 60 minutes using an ultrasonic homogenizer (Branson Model 185) to give an ultrafine fatty emulsion containing Miconazole.

Preparation Example 7-7

To the Miconazole-containing pharmaceutical compositions obtained in Preparation Examples 7-1, 7-4 and 7-5 was added 0.5 g of albumin. Then, freeze-drying treatment was carried out to give freeze-dried preparations.

Test for evaluating the characteristics

The results on characteristic evaluation test of the fat emulsion of the present invention are described below.

In each test, commercially available Miconazole preparation was used for the purpose of comparison. Details of each sample are described below.

Test sample:
  fatty emulsion of the present invention obtained in Preparation Example 7-2

Comparative sample:
  commercially available Miconazole preparation for injection (trademark: FLORID F INJECTION, Mochida Pharmaceutical Co., Ltd.); this is a preparation solubilized using surface active agent HCO-60.

Test Example 8-1:

Change in blood concentration

Using SD strain male rats (body weight, about 250 g) as experimental animals, the test sample and the comparative sample were intravenously administered in the tail vein. The dose administered was 10 mg/kg when calculated as Miconazole. After administration, a small quantity of blood was collected from the jugular vein to obtain plasma. The concentration of Miconazole in blood was determined by high performance liquid chromatography. The results are shown in FIG. 13.

When the test sample was administered, the concentration of Miconazole in plasma was higher than that in the comparative sample. It was shown that the fatty emulsion of the present invention could achieve higher blood concentration as compared to the known preparation.

Test Example 8-2:

Transfer of drug into inflammatory region

It is known that the site infected with fungi causes inflammatory reaction. Therefore, as the model system, transfer of the drug into experimentally induced inflammatory region was evaluated.

Using SD strain male rats (body weight, about 250 g) as experimental animals, 0.1 ml of 2% λ-carrageenin was administered into the thoracic cavity to induce experimental pleurisy. Two hours and a half after, the test sample and the comparative sample were intravenously administered in the tail vein. A dose administered was 10 mg/kg when calculated as Miconazole. After administration, the animal was bled from the abdominal aorta to death to collect the fluid exuded into the thoracic cavity. The concentration of Miconazole in the exuded fluid was determined by high performance liquid chromatography. The results are shown in FIG. 14. When the test sample was administered, the concentration of Miconazole in the exuded fluid was higher than that in the comparative sample. It was shown that the fatty emulsion of the present invention had remarkably collected onto the inflammatory region (infected lesion) and could achieve more effective and safer drug therapy.

Test Example 8-3:

Measurement of particle diameter

The mean particle diameter in Preparation Example 7-2 was approximately 20 to 100 nm. Furthermore, the fatty emulsion of Preparation Example 7-2 did not contain particles of 1µ or more.

It is apparent that the fatty emulsions of the present invention are composed of extremely fine and uniform emulsion particles. Furthermore, it is apparent that effective and safe drug therapy can be realized since particles of 1µ or more which cause problems in toxic consideration are not contained therein in administering the fatty emulsions intravenously.

The present invention also has particular utility in the administration of calcium antagonists. Calcium antagonists are excellent agents for treating hypertension and angina pectoris. Dihydropyridine compounds which are representative of the calcium antagonists have already been used widely in the clinical field.

However, it is difficult to make preparations of dihydropyridine compounds for injection since they are sparingly soluble in water and the preparations for injection have not been provided for clinical use to date. In manufacturing preparations for injection containing drugs which are sparingly soluble in water, there is known a technique which comprises solubilizing such drugs using polyoxyethylene-hardened castor oil (HCO-60) which is known to be the only one surface active agent that can be intravenously administered.

However, it was recently found that this surface active agent HCO-60 caused anaphylaxic shock and was questionable as an additive to drugs. Therefore, its preparations involve problems in that the clinical use is strictly restricted and hence, medical treatment cannot be sufficient.

It has thus been desired to develop safe and effective preparations for injection containing dihydropyridine compounds.

The present inventors have made continuous investigations with attempts to prepare medical preparations containing sparingly water-soluble dihydropyridine compounds without containing any harmful surface active agent such as polyoxyethylene-hardened castor oil (HCO-60), etc. and further to provide preparation forms having excellent transfer of drugs into the site to be acted upon without affecting molecular level pharmacological mechanism possessed by dihydropyridine compounds. As a result, they have finally succeeded in accomplishing the present invention.

The emulsion particles in the fatty emulsions of the present invention have affinity to blood vessels, etc. so that drugs such as dihydropyridine compounds which have activities on circulatory organs or blood vessel system can be efficiently transferred onto the site to be acted upon.

Furthermore, the emulsion particles of smaller than about 100 nm are advantageous in attaining the effect that nonspecific intake by the reticuloendothelial system such as liver, etc. is avoided and blood concentration of the drug can be maintained on a much higher level.

In addition, the fatty emulsions of the present invention have a turbidity so that light stability of the dihydropyridine compound, which is unstable to light, can be improved. This is one of the effects achieved by the present invention.

The preparation comprising the fatty emulsions of the present invention is generally administered intravenously to human or various animals, for purposes of treating or preventing hypertension, angina pectoris, etc., or controlling blood pressure, or the like.

A dose of the preparation comprising the fatty emulsions of the present invention may vary depending upon route for administration, preparation form, condition and purpose but is generally preferably 1 to 1000 ml/time as the emulsion. A dose administered as the dihydropyridine compound is generally 0.1 to 100 mg/time for an adult.

According to the present invention, clinical value of the dihydropyridine compound can be markedly enhanced.

The effects of the present invention can be summarized in overcoming the prior art problems that appropriate, injectable preparations of the dihydropyridine compound could not be prepared and providing novel, safe and more effective preparations of the dihydropyridine compound that (1) pharmacological activity per se of the drug is not affected, (2) the drug is selectively transferred efficiently into lesional tissue, (3) blood concentration of the drug can be maintained over long periods of time, (4) a necessary dose of the drug can be reduced, and (5) no harmful additive is used and as a result, they have finally succeeded in accomplishing the present invention. These effects have been achieved by the present invention for the first time.

The constituent components of the fatty emulsions of the present invention are mainly composed of medically acceptable lipids which have been heretofore used as medicines in the clinical field and therefore can be extremely safe when used. This is also one of the important aspects of the present invention.

EXAMPLES

Hereafter the present invention is explained in more detail, by referring to examples relating to the preparation of the fatty emulsion of the present invention, but the present invention is not deemed to be limited thereto.

Preparation Example 9-1

After 3 mg of Nifedipine, 0.5 g of purified soybean oil and 0.5 g of purified yolk lecithin were mixed with and dissolved in 100 ml of a mixture of chloroform/methanol (1/1, v/v), the solvent was completely removed under reduced pressure using a rotary evaporator. To the residue was added 8 ml of 0.24M glycerine aqueous solution. The mixture was stirred with a homogenizer to form a crude emulsion. By adding 0.24M glycerine aqueous solution to make the volume 10 ml, the mixture was emulsified for 60 minutes under ice-cooling using an ultrasonic homogenizer (Branson Model 185) to give an ultrafine fatty emulsion containing Nifedipine.

Preparation Example 9-2

After 20 mg of Nifedipine, 0.25 g of purified soybean oil and 0.25 g of purified yolk lecithin were mixed with and dissolved in 100 ml of a mixture of chloroform/methanol (1/1, v/v), the solvent was completely removed under reduced pressure using a rotary evaporator. To the residue was added 8 ml of isotonic phosphate buffer solution. The mixture was stirred with a homogenizer to form a crude emulsion. By adding isotonic phosphate buffer solution to make the volume 10 ml, the mixture was emulsified for 60 minutes under ice-cooling using an ultrasonic homogenizer (Branson Model 185) to give an ultrafine fatty emulsion containing Nifedipine.

Preparation Example 9-3

After 2 g of Nifedipine, 20 g of purified soybean oil and 30 g of purified yolk lecithin were heated to about 60° C. to mix them with each other, 500 ml of 0.24M glycerine aqueous solution was added to the mixture. The mixture was stirred with a homomixer to form a crude emulsion. The crude emulsion was emulsified under high pressure using a micro fluidizer to give an ultrafine fatty emulsion containing Nifedipine.

Preparation Example 9-4

After 1 mg of Nifedipine, 0.5 g of cholesteryl oleate and 0.5 g of purified yolk lecithin were mixed with and dissolved in 100 ml of a mixture of chloroform methanol (1/1, v/v), the solvent was completely removed under reduced pressure using a rotary evaporator. To the residue was added 8 ml of 0.24M glycerine aqueous solution. The mixture was stirred with a homogenizer to form a crude emulsion. By adding 0.24M glycerine aqueous solution to make the volume 10 ml, the mixture was emulsified for 60 minutes using an ultrasonic homogenizer (Branson Model 185) to give an ultrafine fatty emulsion containing Nifedipine.

Preparation Example 9-5

After 3 mg of Nifedipine, 0.5 g of purified soybean oil, 0.4 g of purified yolk lecithin and 0.1 g of dimyristoylphosphatidylglycerol were mixed with and dissolved in 100 ml of a mixture of chloroform/methanol (1/1, v/v), the solvent was completely removed under reduced pressure using a rotary evaporator. To the residue was added 8 ml of 9% lactose aqueous solution. The mixture was stirred with a homogenizer to form a crude emulsion. By adding 9% lactose aqueous solution to make the volume 10 ml, the mixture was emulsified for 60 minutes using an ultrasonic homogenizer (Branson Model 185) to give an ultrafine fatty emulsion containing Nifedipine.

Preparation Example 9-6

After 5 mg of Nifedipine, 0.5 g of purified soybean oil, 0.4 g of hydrogenated yolk lecithin and 0.1 g of cholesterol were mixed with and dissolved in 100 ml of a mixture of chloroform/methanol (1/1, v/v), the solvent was completely removed under reduced pressure using a rotary evaporator. To the residue was added 8 ml of 9% lactose aqueous solution. The mixture was stirred with a homogenizer to form a crude emulsion. By adding 9% lactose aqueous solution to make the volume 10 ml, the mixture was emulsified for 60 minutes using an ultrasonic homogenizer (Branson Model 185) to give an ultrafine fatty emulsion containing extremely finely divided Nifedipine.

Preparation Example 9-7

After 3 mg of methyl 2,6-dimethyl-4-(-2nitrophenyl)-5-(2-oxo-1,3,2dioxaphosphorynan-2-y)-1,4-dihydropyridine-3-carboxylate, 0.5 g of purified soybean oil and 0.5 g of purified yolk lecithin were mixed with and dissolved in 100 ml of a mixture of chloroform/methanol (1/1, v/v), the solvent was completely removed under reduced pressure using a rotary evaporator. To the residue was added 8 ml of 0.24M glycerine aqueous solution. The mixture was stirred with a homogenizer to form a crude emulsion. By adding 0.24M glycerine aqueous solution to make the volume 10 ml, the mixture was emulsified for 60 minutes under ice-cooling using an ultrasonic homogenizer (Branson Model 185) to give an extremely finely divided fatty emulsion.

Preparation Example 9-8

To the dihydropyridine compound-containing pharmaceutical compositions obtained in Preparation Examples 9-1, 9-4, 9-5 and 9-7 was added 0.5 g of albumin. Then, freeze-drying treatment was carried out to give freeze-dried preparations.

Measurement of particle diameter

With respect to the particle diameter, the particle diameter was evaluated with a dynamic light scattering particle diameter measuring device using a laser light. The mean particle diameter in Preparation Examples 9-2 and 9-7 was approximately 20 to 100 nm. Furthermore, the fatty emulsion did not contain particles of 1μ or more.

It is apparent that the fatty emulsions of the present invention are composed of extremely fine and uniform emulsion particles. Furthermore, it is apparent that effective and safe drug therapy can be realized since particles of 1μ or more which cause problems in toxic consideration are not contained therein in administering the fat emulsion intravenously.

The present invention also has particular utility in the administration of anti-inflammatory and analgesic substances. As the anti-inflammatory and analgesic substance in accordance with the present invention, oil-soluble anti-inflammatory and analgesic substances which have been used with conventional fat emulsions having a particle diameter of approximately 0.2 μm to about 0.4 μm and which have been used in conventional fatty emulsions and oil-soluble derivatives thereof can be used as they are.

The anti-inflammatory and analgesic substance is at least one selected from the group consisting of Indometacin, Flurbiprofen, 4-biphenyryl acetic acid compounds, aspirin, salicylic acid, methyl salicylate, Ibuprofen, Flufenamic Acid, Ketoprofen and various oil-soluble derivatives of methyl, ethyl, isopropyl, butyl, geranyl, pharnecyl, pamitic acid, cetyl, tocopheryl, glycerol, cholesterol, etc. These substances are all stably carried on the emulsion particles but the oil-soluble derivatives are generally preferred. This is because oil solubility of the drug can be enhanced by leading the drug into these derivatives and a large quantity of the drug can be readily carried in the emulsion particles.

The preparation comprising the fatty emulsions of the present invention is generally administered intravenously to human or various animals, for purposes of treating or preventing various inflammations including rheumatoid, and alleviating pains after operation or various diseases, etc.

Effects

According to the present invention, clinical value of the non-steroidal anti-inflammatory and analgesic substance can be markedly enhanced. The effects of the present invention can be summarized in overcoming the prior art problems and providing novel, safe and more effective preparations of the non-steroidal anti-inflammatory and analgesic substance that (1) pharmacological activity per se of the drug is not affected, (2) the drug can be selectively transferred efficiently into lesional tissue, (3) blood concentration of the drug can be maintained over long periods of time, (4) a necessary dose of the drug can be reduced, and (5) no harmful additive is used and as a result, they have finally succeeded in accomplishing the present invention. These effects have been achieved by the present invention for the first time.

EXAMPLES

Hereafter the present invention is explained in more detail by referring to examples relating to the preparation of the fat emulsion of the present invention, but the present invention is not deemed to be limited thereto.

Preparation Example 10-1

After 0.1 g of palmitic acid ester of methyl salicylate, 2.5 g of purified soybean oil and 1.5 g of purified yolk lecithin were mixed with heating at 40° to 70° C. and, 50 ml of 0.24M glycerine aqueous solution was added to the mixture. The mixture was stirred with a homogenizer to form a crude emulsion. Under ice-cooling, the crude emulsion was emulsified for 60 minutes using an ultrasonic homogenizer (Branson Model 185) to give an extremely fine fatty emulsion.

Preparation Example 10-2

After 1 g of Flurbiprofen, 50 g of purified soybean oil and 50 g of purified yolk lecithin were heated to about 60° C. to dissolve them, 500 ml of 0.24M glycerine aqueous solution was added to the mixture. The mixture was stirred with a homomixer to form a crude emulsion. The crude emulsion was emulsified under high pressure (800 to 1200 kg/cm) using a Manton-Gaulin type homogenizer to give an extremely fine fatty emulsion.

Preparation Example 10-3

After 0.1 g of Ibuprofen, 2 g of purified soybean oil and 3 g of purified yolk lecithin were mixed with and dissolved in 100 ml of a mixture of chloroform/methanol (1/1, v/v), the solvent was Completely removed under reduced pressure using a rotary evaporator. To the residue was added 8 ml of isotonic phosphate buffer solution. The mixture was stirred with a homogenizer to form a crude emulsion. By adding isotonic phosphate buffer solution to make the volume 10 ml, the mixture was emulsified for 60 minutes under ice-cooling using an ultrasonic homogenizer (Branson Model 185) to give an extremely fine fatty emulsion.

Preparation Example 10-4

After 2 g of Indometacin pharnecyl ester, 20 g of purified soybean oil and 18 g of purfied yolk lecithin were heated to about 60° C. to mix them, 100 ml of 0.24M glycerine aqueous solution was added to the mixture. The mixture was stirred with a homomixer to form a crude emulsion. The crude emulsion was emulsified under high pressure using a micro fluidizer to give an extremely fine fatty emulsion.

Preparation Example 10-5

After 0.1 g of Ibuprofen methyl ester, 0.5 g of cholesteryl oleate and 0.5 g of purified yolk lecithin were mixed with and dissolved in 100 ml of a mixture of chloroform/methanol (1/1, v/v), the solvent was completely removed under reduced pressure using a rotary evaporator. To the residue was added 8 ml of 0.24M glycerine aqueous solution. The mixture was stirred with a homogenizer to form a crude emulsion. By adding 0.24M glycerine aqueous solution to make the volume 10 ml, the mixture was emulsified for 60 minutes using an ultrasonic homogenizer (Branson Model 185) to give an extremely fine fatty emulsion.

Preparation Example 10-6

After 50 mg of ethyl 4-biphenyrylacetate, 0.5 g of purified soybean oil, 0.4 g of purified yolk lecithin and 0.1 g of dimyristoylphosphatidylglycerol were mixed with and dissolved in 100 ml of a mixture of chloroform/methanol (1/1, v/v), the solvent was completely removed under reduced pressure using a rotary evaporator. To the residue was added 8 ml of 9% lactose aqueous solution. The mixture was stirred with a homogenizer to form a crude emulsion. By adding 9% lactose aqueous solution to make the volume 10 ml, the mixture was emulsified for 60 minutes using an ultrasonic homogenizer (Branson Model 185) to give an extremely fine fatty emulsion.

Preparation Example 10-7

After 50 mg of Ibuprofen geranyl ester, 0.5 g of purified soybean oil, 0.4 g of hydrogenated yolk lecithin and 0.1 g of cholesterol were mixed with and dissolved in 100 ml of a mixture of chloroform/methanol (1/1, v/v), the solvent was completely removed under reduced pressure using a rotary evaporator. To the residue was added 8 ml of 9% lactose aqueous solution. The mixture was stirred with a homogenizer to form a crude emulsion. By adding 9% lactose aqueous solution to make the volume 10 ml, the mixture was emulsified for 60 minutes using an ultrasonic homogenizer (Branson Model 185) to give an extremely fine fatty emulsion.

Preparation Example 10-8

After 50 mg of cholesteryl acetylsalicylate, 0.5 g of purified soybean oil and 0.4 g of purified yolk lecithin were mixed with and dissolved in100 ml of a mixture of chloroform/methanol (1/1, v/v), the solvent was completely removed under reduced pressure using a rotary evaporator. To the residue was added 8 ml of 0.24M glycerine aqueous solution. The mixture was stirred with a homogenizer to form a crude emulsion. By adding 0.24M glycerine aqueous solution to make the volume 10 ml, the mixture was emulsified for 60 minutes using an ultrasonic homogenizer (Branson Model 185) to give an extremely fine fatty emulsion.

Preparation Example 10-9

After 0.1 g of glyceryl tribiphenylacetate, 0.5 g of cholesteryl oleate and 0.5 g of purified yolk lecithin were mixed with and dissolved in 100 ml of a mixture of chloroform/methanol (1/1, v/v), the solvent was completely removed under reduced pressure using a rotary evaporator. To the residue was added 8 ml of 0.24M glycerine aqueous solution. The mixture was stirred with a homogenizer to form a crude emulsion. By adding 0.24M glycerine aqueous solution to make the volume 10 ml, the mixture was emulsified for 60 minutes using a ultrasonic homogenizer (Branson Model 185) to give an extremely fine fatty emulsion.

Preparation Example 10-10

To the non-steroidal anti-inflammatory and analgesic substance-containing pharmaceutical compositions obtained in Preparation Examples 10-1, 10-5 and 10-6 was added 0.5 g of albumin. Then, freeze-drying treatment was carried out to give freeze-dried preparations.

Measurement of particle diameter

With respect to the particle diameter of the fat emulsions in Preparation Examples 10-2 and 10-5, the particle diameter was evaluated with a dynamic light scattering particle diameter measuring device using a laser light.

As the result, the particle diameter was approximately 15 to 100 nm. Furthermore, the fatty emulsion did not contain particles of 1μ or more.

It is apparent that the fat emulsion of the present invention is composed of extremely fine and uniform emulsion particles. Furthermore, it is apparent that effective and safe drug therapy can be realized since particles of 1μ or more which cause problems in toxic consideration are not contained therein in administering the fatty emulsion intravenously.

The present invention also has particular utility in the adminstration of mitomycin C. Mitomycin C has excellent anti-cancer activity and has been widely used in the clinical field. However, mitomycin C encounters difficulties in that mitomycin C has many serious side effects and clinical application of its preparations has been extremely restricted and hence, satisfactory drug therapy is impossible. It has thus been desired to improve transfer of mitomycin C to the tumor site and alleviate side effects.

Heretofore, screening has been made with respect to various derivatives of mitomycin C and at the same time, in order to solve the foregoing problems by means of pharmaceutical preparations represented by liposome preparations, various efforts have been made on mitomycin C derivatives represented by general formula [I] (for example, nonyloxycarbonyl mitomycin C) which are prodrugs of mitomycin C.

Liposome preparations of the mitomycin C derivatives described above rapidly release drugs therefrom after administration and the drugs are readily metabolized so that any satisfactory improving effect of anti-cancer activity is not obtained. Therefore, further improvement has been desired.

Many investigations have been hitherto made on pharmaceutical preparations for improving transfer of drugs in blood or from the site applied into the lesional tissue. A method for utilizing drugs enveloped in the aforesaid liposome prepared from phospholipids involve defects that: (1) liposome having an aqueous phase enveloped with a lipid bilayer has many problems in stability during storage, (2) the mitomycin C derivatives described above are highly oil-soluble and when the mitomycin C derivatives are prepared in the form of liposome preparations, they are present in phospholipid bimolecular membrane and thus injure liposome membrane structure to fail to stably keep drugs, and the like.

This is considered to be because liposome has such a structure that the inner aqueous layer is separated from the outer aqueous layer by the phospholipid dimolecular membrane so that the structure would be unstable to various forces. It is also known that an increased particle diameter because of flocculation would be disadvantageous during storage.

The mitomycin C derivatives in accordance with the present invention are represented by the following general formula [I]:

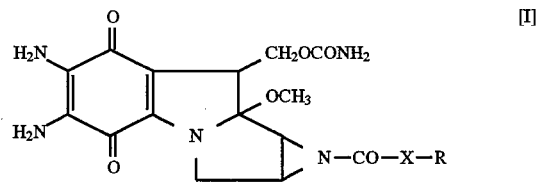

wherein X represents $-(CH_2)_n-O-$ or $-(CH_2)_n-NHCOO-$; n represents an integer of 0 to 4; and R represents a straight or branched chain or cyclic, saturated or unsaturated hydrocarbon having 3 to 25 carbon atoms.

Examples of R include isobutyl, nonyl, cetyl, geranyl, cholesteryl, etc. but R is not limited thereto.

Of the compounds represented by general formula [I] in accordance with the present invention, compounds except for alkyloxycarbonyl mitomycin C derivatives (compounds of general formula [I] wherein x is $-(CH_2)_n-O-$ and n is 0) and mitomycin C derivatives of general formula [I] wherein R is cholesteryl (for example, N-cholesteryloxycarbonylglycyl mitomycin C, cholesteryloxyacetyl mitomycin C, etc.) are novel compounds which are not found in the literature, and have been found by the present inventors for the first time.

The compounds represented by general formula [I] are particularly excellent in formation of free mitomycin C in human plasma or tumor cells. The mitomycin C derivatives per se have no activity but exhibit their activity because they are metabolized to mitomycin C, which is an active form, in the living body including tumor.

According to the present invention, clinical value of the mitomycin C derivative can be markedly enhanced. The effects of the present invention can be summarized in providing novel, safe and more effective preparations of the mitomycin C derivative by overcoming the prior art problems described above, improving the anti-tumor effect and markedly reducing side effects (toxicity) which are the most serious clinical problem. These effects have been achieved by the present invention for the first time.

The constituent components of the fatty emulsions of the present invention are mainly composed of medically acceptable lipids which have been heretofore used as medicines in the clinical field and therefore, can be used safely.

EXAMPLES

Hereafter the present invention is explained in more detail by referring to examples relating to the preparation of the fat emulsion of the present invention, but the present invention is not deemed to be limited thereto.

Preparation Example 11-1

After 2 g of nonyloxycarbonyl mitomycin C, 0.5 g of purified soybean oil and 0.5 g of purified yolk lecithin were mixed and dissolved in 100 ml of a chloroform/methanol (1/1, v/v) mixture, the solvent was completely removed with a rotary evaporator under reduced pressure. To the residue was added 8 ml of 0.24 glycerine aqueous solution. The mixture was stirred with a homogenizer to form a crude emulsion. After 0.24M glycerine aqueous solution was added to the emulsion to make the volume 10 ml, the mixture was emulsified for 60 minutes using an ultrasonic homogenizer (Branson Model 185) under ice-cooling to give an ultrafine fatty emulsion containing mitomycin C derivative.

Preparation Example 11-2

After 40 mg of nonyloxycarbonyl mitomycin C, 0.5 g of purified soybean oil and 0.5 g of purified yolk lecithin were mixed and dissolved in 100 ml of a chloroform/methanol (1/1, v/v) mixture, the solvent was completely removed with a rotary evaporator under reduced pressure. To the residue was added 8 ml of isotonic phosphate buffer. The mixture was stirred with a homogenizer to form a crude emulsion. After isotonic phosphate buffer was added to the emulsion to make the volume 10 ml, the mixture was emulsified for 60 minutes using an ultrasonic homogenizer (Branson Model 185) under ice-cooling to give an ultrafine fatty emulsion containing mitomycin C derivative.

Preparation Example 11-3

After 2 g of N-(cholesteryloxycarbonyl)glycyl mitomycin C, 20 g of purified soybean oil and 25 g of purified yolk lecithin were heated to about 60° C. to mix them, 100 ml of 0.24M glycerine aqueous solution was added to the mixture. The mixture was stirred with a homomixer to form a crude emulsion. The crude emulsion was emulsified with a microfluidizer under high pressure to give an ultrafine fatty emulsion containing extremely fine mitomycin C derivative.

Preparation Example 11-4

After 1 mg of nonyloxycarbonyl mitomycin C, 0.5 g of cholesteryl oleate and 0.5 g of purified yolk lecithin were mixed and dissolved in 100 ml of a chloroform/methanol (1/1, v/v) mixture, the solvent was completely removed with a rotary evaporator under reduced pressure. To the residue was added 8 ml of 0.24M glycerine aqueous solution. The mixture was stirred with a homogenizer to form a crude emulsion. After 0.24M glycerine aqueous solution was added to the emulsion to make the volume 10 ml, the mixture was emulsified for 60 minutes using an ultrasonic homogenizer (Branson Model 185) to give an ultrafine fatty emulsion containing mitomycin C derivative.

Preparation Example 11-5

After 3 mg of cholesterylacetyl mitomycin C, 0.5 g of purified soybean oil, 0.4 g of purified yolk lecithin and 0.1 g of dimyristoylphosphatidylglycerol were mixed and dissolved in 100 ml of a chloroform/methanol (1/1, v/v) mixture, the solvent was completely removed with a rotary evaporator under reduced pressure. To the residue was added 8 ml of 9% lactose aqueous solution. The mixture was stirred with a homogenizer to form a crude emulsion. After 9% lactose aqueous solution was added to the emulsion to make the volume 10 ml, the mixture was emulsified for 60 minutes using an ultrasonic homogenizer (Branson Model 185) to give an ultrafine fatty emulsion containing mitomycin C derivative.

Preparation Example 11-6

After 5 mg of nonyloxycarbonyl mitomycin C, 0.5 g of purified soybean oil, 0.4 g of hydrogenated yolk lecithin and 0.1 g of cholesterol were mixed and dissolved in 100 ml of a chloroform/methanol (1/1, v/v) mixture, the solvent was completely removed with a rotary evaporator under reduced pressure. To the residue was added 8 ml of 9% lactose aqueous solution. The mixture was stirred with a homogenizer to form a crude emulsion. After 9% lactose aqueous solution was added to the emulsion to make the volume 10 ml, the mixture was emulsified for 60 minutes using an ultrasonic homogenizer (Branson Model 185) to give an ultrafine fatty emulsion containing mitomycin C derivative.

Preparation Example 11-7

N-(Nonyloxycarbonyl)glycyl mitomycin C was obtained by the following synthesis method.

A solution of 824 mg of nonyl chlorocarbonate in 20 ml of dioxan was dropwise added to a solution of 300 mg of glycine and 808 mg of triethylamine in 3 ml of water at 0° C. After stirring for 3 hours, the reaction solution was concentrated under reduced pressure and 10 ml of 1N hydrochloric acid was added to the residue. The formed precipitates were extracted with 20 ml of chloroform. The organic phase was washed with 10 ml of water and then dried over magnesium sulfate. After concentrating under reduced pressure, 570 mg of white crystals (N-(nonyloxycarbonyl)glycine) was obtained. The crystals were dissolved in a mixture of 10 ml of dioxan and 2 ml of chloroform and 270 mg of N-hydroxysuccinimide and 470 mg of dicyclohexylcarbodiimide were added to the solution at 0° C. After allowing to stand at 4° C. for 12 hours, the formed precipitates were filtered off and the filtrate was concentrated under reduced pressure to give 772 mg of colorless oily residue.

At room temperature, 150 mg of the oily residue described above and 36 mg of pyridine were added to a solution of 150 mg of mitomycin C in 5 ml of N,N-dimethylformamide followed by stirring for 4 hours. After the reaction solution was concentrated under reduced pressure, the residue was dissolved in 20 ml of chloroform. The solution was washed with 15 ml of water. After drying over magnesium sulfate, the organic phase was concentrated under reduced pressure to give red purple residue. The residue was passed through a silica gel column, which was eluted with a mixture of chloroform/methanol. The eluted red purple fraction was concentrated under reduced pressure to give 225 mg (yield, 89%) of red purple crystals (N-(nonyloxycarbonyl)glycyl mitomycin C) (melting point: 250° C. or higher (decomposed)).

FAB-MS spectrum of this compound showed m/z; 563 (M+2) and $^1$H-NMR spectrum showed the following peaks, which enabled to confirm its structure.

δ: 5.36–5.08 (3H, m, —COCH$_2$NHCOO—, NH2) 4.43 (1H, d, J=13.5 Hz, 3-H) 4.16–3.89 (4H, m, —COCH$_2$NH—, —COOCH$_2$—) 3.71 (1H, dd, J=10.8, 10.8 Hz 10-H) 3.59 (1H, d, J=4.6 Hz 10-H) 3.57 (1H, dd, J=1.6, 13.5 Hz 3'-H) 3.48 (1H, dd, J=1.6, 4.6 Hz 2-H) 3.18 (3H, s, OCH$_3$) 1.78 (3H, s, —C%C—CH$_3$) 1.66–1.48 (2H, m, —COOCH$_2$CH$_2$—) 1.42–1.16 (12H, m, —CH$_2$(CH$_2$)$_6$CH$_3$) 0.88 (3H, t, J=7 Hz, —(CH$_2$)$_8$CH$_3$)

After 3 mg of the thus obtained N-(nonyloxycarbnyl) glycyl mitomycin C, 0.5 g of purified soybean oil and 0.5 g of purified yolk lecithin were mixed and dissolved in 100 ml of a chloroform/methanol (1/1, v/v) mixture, the solvent was completely removed with a rotary evaporator under reduced pressure. To the residue was added 8 ml of 0.24 glycerine aqueous solution. The mixture was stirred with a homogenizer to form a crude emulsion. After 0.24 glycerine aqueous solution was added to the emulsion to make the volume 10 ml, the mixture was emulsified for 60 minutes using an ultrasonic homogenizer (Branson Model 185) under ice-cooling to give an ultrafine fatty emulsion containing mitomycin C derivative.

Preparation Example 11-8

N-(Isobutyloxycarbonyl)glycy mitomycin C was obtained by the following synthesis method.

A solution of 544 mg of isobutyl chlorocarbonate in 20 ml of dioxan was dropwise added to a solution of 300 mg of glycine and 808 mg of triethylamine in 3 ml of water at 0° C. After stirring for 3 hours, the reaction solution was concentrated under reduced pressure and 10 ml of 1N hydrochloric acid was added to the residue. The formed precipitates were extracted with 20 ml of chloroform. The organic phase was washed with 10 ml of water and then dried over magnesium sulfate. After concentrating under reduced pressure, 409 mg of white crystals (N-(isobutyloxycarbonyl)glycine) was obtained.

The crystals were dissolved in a mixture of 10 ml of dioxan and 2 ml of chloroform and 270 mg of N-hydroxysuccinimide and 470 mg of dicyclohexylcarbodiimide were added to the solution at 0° C. After allowing to stand at 4° C. for 12 hours, the formed precipitates were filtered off and the filtrate was concentrated under reduced pressure to give 772 mg of colorless oily residue.

At room temperature, 150 mg of the oily residue described above and 36 mg of pyridine were added to a solution of 150 mg of mitomycin C in 5 ml of N,N-dimethylformamide followed by stirring for 4 hours. After the reaction solution was concentrated under reduced pressure, the residue was dissolved in 20 ml of chloroform. The solution was washed with 15 ml of water. After drying over magnesium sulfate, the organic phase was concentrated under reduced pressure to give red purple residue. The residue was passed through a silica gel column, which was eluted with a mixture of chloroform/methanol. The eluted red purple fraction was concentrated under reduced pressure to give 161 mg (yield, 73%) of red purple crystals (N-isobutyloxycarbonyl)glycyl mitomycin C) (melting point: 250° C. or higher (decomposed)).

After 3 mg of the thus obtained N-(isobutyloxycarbonyl) glycyl mitomycin C, 0.5 g of purified soybean oil and 0.5 g of purified yolk lecithin were mixed and dissolved in 100 ml of a chloroform/methanol (1/1, v/v) mixture, the solvent was completely removed with a rotary evaporator under reduced pressure. To the residue was added 8 ml of 0.24 fl glycerine aqueous solution. The mixture was stirred with a homogenizer to form a crude emulsion. After 0.24 glycerine aqueous solution was added to the emulsion to make the volume 10 ml, the mixture was emulsified for 60 minutes using an ultrasonic homogenizer (Branson Model 185) under ice-cooling to give an ultrafine fatty emulsion containing mitomycin C derivative.

Preparation Example 11-9

N-Cetyloxyacetyl mitomycin C was obtained by the following synthesis method.

Cetyl alcohol (1.2 g) and ethylene glycol (10 ml) were added to benzene (100 ml) and p-toluenesulfonic acid monohydrate (100 mg) was further added to the mixture following by refluxing for 8 hours. The reaction mixture was concentrated under reduced pressure. After the residue was extracted with ether, the extract was washed with saturated sodium hydrogencarbonate solution. The organic phase was dried over magnesium sulfate and concentrated under reduced pressure to give the residue. Lithium aluminum hydroxide (0.5 g) and aluminum chloride (2 g) were dissolved in dry ether (50 ml) and the ethereal solution of the residue described above was dropwise added to the solution. Stirring was continued for 4 hours. After a small quantity of diluted sulfuric acid was added to the mixture, insoluble matters were filtered off and the ethereal layer was washed with water and then with 5 sodium hydrogencarbonate. After drying over magnesium sulfate, the ethereal layer was concentrated under reduced pressure to give the residue. The oily residue was oxidized with Jones reagent to give cetyl oxyacetate.

The thus obtained cetyl oxyacetate was bound to mitomycin C using N-hydroxysuccinimide in a manner similar to Preparation Example 11-7 to give cetyloxyacetyl mitomycin C (melting point: 11°–120° C. (decomposed)).

After 3 mg of the thus obtained N-cetyloxyacetyl mitomycin C, 0.5 g of purified soybean oil and 0.5 g of purified yolk lecithin were mixed and dissolved in 100 ml of a chloroform/methanol (1/1, v/v) mixture, the solvent was completely removed with a rotary evaporator under reduced pressure. To the residue was added 8 ml of 0.24M glycerine aqueous solution. The mixture was stirred with a homogenizer to form a crude emulsion. After 0.24M glycerine aqueous solution was added to the emulsion to make the volume 10 ml, the mixture was emulsified for 60 minutes using an ultrasonic homogenizer (Branson Model 185) under ice-cooling to give an ultrafine fatty emulsion containing mitomycin C derivative.

Preparation Example 11-10

N-(Geranyloxycarbonyl)glycyl mitomycin C was synthesized in a manner similar to Preparation Example 11-8 except that the same mole of geranyl chlorocarbonate was used in place of nonyl chlorocarbonate in Preparation Example 11-7 (melting point, 250° C. or higher (decomposed)). After 40 mg of the thus obtained mitomycin C derivative, 0.5 g of purified soybean oil and 0.5 g of purified yolk lecithin were mixed and dissolved in 100 ml of a chloroform/methanol (1/1, v/v) mixture, the solvent was completely removed with a rotary evaporator under reduced pressure. To the residue was added 8 ml of isotonic phosphate buffer. The mixture was stirred with a homogenizer to form a crude emulsion. After isotonic phosphate buffer was added to the emulsion to make the volume 10 ml, the mixture was emulsified for 60 minutes using an ultrasonic homogenizer (Branson Model 185) under ice-cooling to give an ultrafine fatty emulsion containing mitomycin C derivative.

Preparation Example 11-11

To the fatty emulsions obtained in Preparation Examples 11-1, 11-4, 11-5 and 11-7 was added 0.5 g of albumin. The mixtures were subjected to a freeze-drying treatment to give dry preparations.

The results of test of the fatty emulsions in accordance with the present invention on property evaluation are shown below.

In Test Example 12-1, Test Example 12-2 and Test Example 12-3, the fat emulsion of the present invention obtained in Preparation Example 12-2 was used as a test specimen. In Test Example 12-4, the fat emuslion of the present invention obtained in Preparation Example 12-3 was used as a test specimen.

For purpose of comparison, commercially available mitomycin C injection (Mitomycin C Kyowa S (registered trademark), Kyowa Hakko) was used as a comparative specimen.

Test Example 12-1:

Evaluation on Toxicity

As experimental animals, ddY strain male mice (body weight of about 30 g) were used and the test specimen or the comparative specimen was intravenously administered in the tail vein. A dose was set in 5 mg/kg when calculated as free mitomycin C. The administration was made 3 times in total every other day. Four days after the final administration, a mean body weight of mice is shown in Table 5-1.

In the mice administered with the test specimen, body weight increased normally as in the intact group and no toxicity was observed. However, in the mice administered with the comparative specimen, body weight markedly decreased and serious damage was noted in the digestive tract.

TABLE 5-1

Evaluation of Toxicity by Body Weight Change

| | Mean Body Weight of Mice (g) |
|---|---|
| Intact | 34.0 |
| Test specimen | 33.6 |
| Comparative specimen | 22.0 |

In the fatty emulsion of the present invention, the toxicity was markedly reduced as compared to conventional mitomycin C preparation. It is thus clear that safer drug therapy can be achieved.

Test Example 12-2:
Evaluation of anti-tumor activity

As experimental animals, CDF1 strain male mice (body weight of about 20 g) were used. After P 388 tumor cells were intraperitoneally administered (transplanted), the test specimen or the comparative specimen was intravenously administered in the tail vein. A dose was set in 5 mg/kg/time when calculated as free mitomycin C. In the control group, physiological saline was intravenously administered in a similar manner. The effect of increased life span (ILS) of each compound determined by comparing with the control group is shown in Table 5-2.

TABLE 5-2

Antitumor Effect

| | Increased Life Span (ILS %) |
|---|---|
| Test specimen | 75.8 |
| Comparative specimen | 16.5 |

It is noted that the antitumor effect (increased life span) on the test specimen is markedly excellent as compared to the comparative specimen.

It is evident that the fatty emulsions of the present invention showed a remarkable antitumor effect (increased life span) as compared to conventionally known mitomycin C preparation and more effective and safer drug therapy can be achieved.

Test Example 12-3:
Change in blood concentration

As experimental animals, CDF1 strain male mice (body weight of about 25 g) were used. The test specimen and the comparative specimen were intravenously administered in the tail vein. A dose was set in 5 mg/kg when calculated as free mitomycin C. One, thirty and sixty minutes after the administration, a small quantity of blood was collected. The concentration of mitomycin C in blood was determined by high performance liquid chromatography. The results are shown in Table 5-3.

TABLE 5-3

Blood Concentration (μg/ml)

| | 1 minute after | 30 minutes after | 60 minutes after |
|---|---|---|---|
| Test specimen | 0.1 | 0.6 | 0.5 |
| Comparative specimen | 4.5 | 0.4 | 0.1 |

(mean value, n = 3)

It is revealed that change in concentration of mitomycin C in blood when the test specimen was administered was maintained on a higher level than in the comparative specimen.

It is evident that the fatty emulsions of the present invention can maintain blood concentration of mitomycin C as compared to conventionally known mitomycin C preparation.

Furthermore, the extremely high mitomycin C concentration immediately after the comparative specimen was administered was not observed with the test specimen. This was desirable also in view of toxicity.

Test Example 12-4:
Transfer of drug into tumor site

As experimental animals, ddY strain male mice (body weight of about 25 g) were used. Approximately 10 days after subcutaneous administration of S-180 tumor cells, the test specimen or the comparative specimen was intravenously administered in the tail vein. A dose was set in 5 mg/kg when calculated as free mitomycin C. Thirty minutes after solid tumor was withdrawn and homogenized. The total mitomycin C concentration (calculated as mitomycin C) in the tumor was determined by high performance liquid chromatography. The results are shown in Table 5-4.

TABLE 5-4

Total Mitomycin & Concentration in Tumor

| | Total Mitomycin C Concentration |
|---|---|
| Test specimen | 0.84 ± 0.22 |
| Comparative specimen | 0.15 ± 0.08 |

(mean ± standard deviation, n = 3)

It is shown that when the test specimen was administered, the concentration of mitomycin C in the tumor was higher than in the comparative specimen.

It is evident that the fatty emulsions of the present invention are remarkably accumulated on the tumor site as compared to conventionally known mitomycin C preparation and more effective and safer drug therapy can be achieved.

Test Example 12-5:
Formation of mitomycin C from mitomycin C derivatives

Formation of mitomycin C from nonyloxycarbonyl mitomycin C (derivative 1), N-(nonyloxycarbonyl)glycyl mitomycin C (derivative 2) and N-(cholesteryloxycarbonyl) glycyl mitomycin C (derivative 3) is shown in Table 5-5.

S-180 solid tumor subcutaneously grown in ddY strain mice and human-derived solid tumor cells (MX-1) subcutaneously grown in nude mice were withdrawn and 10% homogenate of each tumor was prepared using isotonic phosphate buffered saline. Each of the mitomycin C derivatives was added to the homogenate in a final concentration of 10 μm. After incubation at 37° C. for 60 minutes, free mitomycin C was determined by high performance liquid chromatography.

It is clear that any of the mitomycin C derivatives forms free mitomycin C in the tumor which is an active form. The formation of free mitomycin C fully corresponds to the quantitative relation with decomposition of the derivatives added.

It was confirmed that these derivatives had the property of mitomycin C as a pro drug.

Furthermore, a rate of forming free mitomycin C varies depending upon the respective derivatives. N-(Nonyloxycarbonyl)glycyl mitomycin C (derivative 2) released mitomycin C more rapidly than derivative 1 and derivative 3. This was similarly noted also in human-derived tumor cells.

TABLE 5-5

| | Formation of Mitomycin C (%) | |
|---|---|---|
| | S-180 | MX-1 |
| Derivative 1 | 3.0 | 5.7 |
| Derivative 2 | 16.0 | 11.4 |
| Derivative 3 | 10.7 | 8.3 |

Test Example 12-6:
Measurement of particle diameter

With respect to the particle diameter of the fat emulsions in Preparation Examples 11-3, the particle diameter was evaluated with a dynamic light scattering particle diameter measuring device using a laser light.

As the result, a mean particle diameter was approximately 20 to 100 nm in Preparation Example 11-3 and the fatty emulsion did not contain particles of 1μ or more.

It is apparent that the fatty emulsions of the present invention are composed of extremely fine and uniform emulsion particles and does not contain particles of 1μ or more which come into problem in toxic consideration so that effective and safe drug therapy can be realized.

Liver Perfusion Test

The single-pass liver perfusion method is usually used for evaluation of drug deliver to liver.

Reference litereature for the single-pass liver perfusion method includes Kiwada et al, *Chem. Pharm. Bull.*, 34:1249–1256 (1986); Sato et al, *J. Pharm. Sci.*, 78:11-16 (1989); Kiwada et al and Sato et al modified surgical operational method of Mortimore et al *Diabetes*, 8: 307–314 (1959), on the rat liver. They injected test sample which contains drug to the liver through the portal vein and then recovered the drug from the vein of the liver and were able to calculate accurately the rate of recovery amount against the injected amount.

The reduced uptake by the liver is demonstrated in detail in FIGS. 15 and 16 and the data disclosed therein.

Male Sprague-Dawley rats (Ca. 250 g) were used in the liver perfusion test. Perfusion of the rat liver was carried out using the conventional method as described below. The rats were anesthetized by intraperitoneal injection of sodium pentobarbital (50 mg/kg), the abdomen and chest were opened, and the portal vein and the inferior vena cava were cannulated with a polyethylene tubing (PE-160). Diluted rat whole blood with Krebs-Ringer bicarbonate buffer containing small amount of heparin, pH 7.4 (1:1, v/v) was aerated with 95% $O_2$:5% $CO_2$ and pumped at 37° C. into the cannulate portal vein with the aid of a peristaltic pump at a rate of 8 mL/min. Ten minutes after the start of perfusion, 0.2 mL of the preparation containing 16 μg of dexamethasone palmitate (Sample A, B and D) or 0.4 mg of egg phosphatidyl choline (Sample C) was rapidly injected at the portal vein side. Immediately after injection, the outflow from vena cava was collected into weighed test tubes in fractions of 3 drops each. The sample volume was calculated from the gain in weight of the tube. The sample was subjected to assay for determination of the recovery from the liver. The recovery means percent of the drug recovered from the liver outflow to the injected amount into the liver.

The present application discloses, for the first time, pharmaceutical microemulsions with extremely reduced uptake by the liver. This is a unique and useful feature of the present invention.

In the present invention, it is not necessary to operate the differential centrifugation, and thus by the present invention, even-sized homogeneous pharmaceutical microemulsions are obtained, as demonstrated by FIG. 17. Samples are the same in FIGS. 15 and 16.

Single-pass liver perfusion ratio is the most common and objective experimental method to measure the uptake by the liver.

The uptake by the liver is determined by the single-pass liver perfusion method. According to the present invention, the uptake by the liver in this evaluation procedure is less than 50%, preferably less than 40% of injected dose per liver.

What is claimed is:

1. A fatty emulsion of particles useful for drug delivery upon parenteral administration, said particles not being liposomes, wherein said particles have a mean particle diameter of from about 16 nm to about 48 nm and contain a therapeutically selective amount of a pharmaceutically acceptable drug selected from the group consisting of an anti-inflammatory agent, an analgesic, an anti-allergic agent, an antibiotic, a chemotherapeutic agent, an anti-cancer agent, an anti-viral agent, an anti-atherosclerosis agent, an anti-lipemic agent, an anti-ulcer agent, an immunoregulator, a vaccine, a radical scavenger, a bronchodilator, a hypnotic, a tranquilizer, a topical anesthetic, and a calcium antagonist, each said particle consisting essentially of a core and a surface layer covering said core, wherein (a) said core consists essentially of a lipid selected from the group consisting of refined soybean oil, cotton seed oil, linseed oil, sesame oil, corn oil, peanut oil and safflower oil, triolein, trilinolein, tripalmitin, tristearin, trimyristin, triarachidonin, and a cholesterol ester, the amount of said core in the emulsion particle ranging from 30 to 85% w/w, and (b) said surface layer consisting essentially of a lipid selected from the group consisting of a phospholipid, a glycolipid, a stearyl glucoside, stearyl amine, and dicetyl phosphate, the amount of said surface layer in the emulsion particle ranging from 15 to 70% w/w.

2. The fatty emulsion of claim 1, wherein the drug is selected from the group consisting of a calcium antagonist, an anti-inflammatory agent, an analgesic, an anti-cancer agent, a chemotherapeutic agent, and anti-bacterial agent.

3. The fatty emulsion of claim 1, wherein the drug is amphotericin B.

4. The fatty emulsion of claim 1, wherein the core consists essentially of a lipid selected from the group consisting of cholesteryl oleate, cholesteryl linoleate, cholesteryl myristate, cholesteryl palmitate, and cholesteryl arachidonate.

5. The fatty emulsion of claim 4, wherein the drug is amphotericin B.

6. The fatty emulsion of claim 1, wherein the surface layer consists essentially of a lipid selected from the group consisting of a phospholipid and a glycolipid.

7. The fatty emulsion of claim 1, wherein the surface layer consists essentially of a lipid selected from the group consisting of lecithin, phosphatidyl choline, and phosphatidic acid.

8. The fatty emulsion of claim 1, wherein the core comprises refined soybean oil and the surface layer comprises yolk lecithin.

* * * * *